United States Patent [19] [11] Patent Number: 4,740,230
Takematsu et al. [45] Date of Patent: Apr. 26, 1988

[54] TRIAZINE DERIVATIVES, AND HERBICIDES CONTAINING THE DERIVATIVES AS THE EFFECTIVE COMPONENT

[75] Inventors: Tetsuo Takematsu, Utsunomiya; Masahiro Nishii, Ichihara; Izumi Kobayashi, Sodegaura, all of Japan

[73] Assignee: Idemitsu Kosan Company Limited, Tokyo, Japan

[21] Appl. No.: 903,682

[22] Filed: Sep. 4, 1986

[30] Foreign Application Priority Data

Sep. 13, 1985 [JP] Japan ................................. 60-201736
Jul. 16, 1986 [JP] Japan ................................. 61-165499

[51] Int. Cl.$^4$ ................. C07D 409/12; C07D 407/12; A01N 43/70
[52] U.S. Cl. .......................................... 71/90; 71/93; 544/209
[58] Field of Search .................. 544/209; 71/90, 93

[56] References Cited

U.S. PATENT DOCUMENTS 3,753,986 8/1973 Singhal et al. ...................... 544/209

FOREIGN PATENT DOCUMENTS 1017862 1/1966 United Kingdom ................ 544/207

Primary Examiner—John M. Ford
Attorney, Agent, or Firm—Frishauf, Holtz, Goodman & Woodward

[57] ABSTRACT

A triazine derivative represented by the general formula:

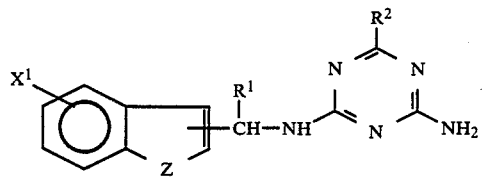

or the general formula:

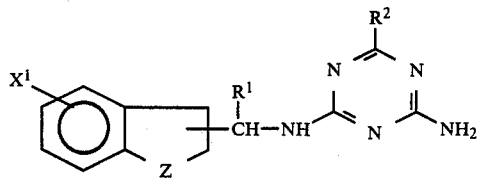

(wherein $X^1$ represents a hydrogen atom, a halogen atom an alkyl group having 1 to 4 carbon atoms or an alkoxyl group having 1 to 4 carbon atoms, Z represents an oxygen atom or a sulfur atom, $R^1$ represents an alkyl group having 1 to 4 carbon atom, and $R^2$ represents a halogen atom, an alkylthio group having 1 to 4 carbon atoms, or an alkoxyl group having 1 to 4 carbon atoms).

This invention also provides a process for efficiently preparing said triazine derivative and a herbicide containing said triazine derivative as a herbicidally effective component.

29 Claims, No Drawings

TRIAZINE DERIVATIVES, AND HERBICIDES CONTAINING THE DERIVATIVES AS THE EFFECTIVE COMPONENT

FIELD OF THE INVENTION

The present invention relates to novel triazine derivatives, a process for preparing the triazine derivatives, and herbicides containing the derivatives as the herbicidally effective component.

BACKGROUND OF THE INVENTION

Various triazine-based herbicides have heretofore been known. For example, 2-methylthio-4,6-bis(alkylamino)-s-triazine derivatives are known to be effective herbicides having a high weed control activity. However, the effect of 2-methylthio-4,6-bis(ethylamino)-s-triazine, for example, greatly varies with conditions such as the type of soil and temperature. In more detail, when used in a mild district, it causes phytotoxicity (injury) even in the commonly used amount, and in a cold district, its effect is exhibited only insufficiently. Thus 2-methylthio-4,6-bis(ethylamino)-s-triazine has a disadvantage in that it can be applied as a herbicide only in a limited district.

The present invention is intended to overcome the above problems and an object of the present invention is to provide a process for preparing a novel herbicide which can exhibit its herbicidal activity nearly equal under various soil and temperature conditions, and also can exhibit its herbicidal activity against various annual weeds and perennial weeds while causing no injury against paddy rice plants and furthermore causing no injury against upland field crops such as corn, oats, wheat, barley and grain sorghum.

As a result of extensive investigations, it has been found that the above objects can be attained by using specified triazine derivatives having a benzofuranyl or thianaphthenyl group, or a dihydrobenzofuranyl or dihydrothianaphthenyl group.

SUMMARY OF THE INVENTION

The present invention relates to a triazine derivative represented by the general formula (I):

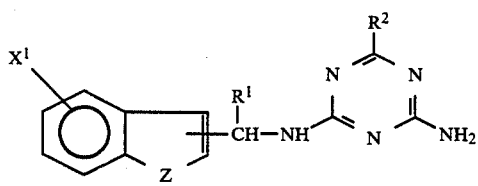

or the general formula (II):

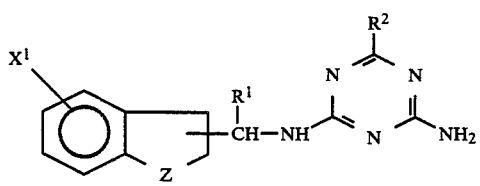

(wherein $X^1$ represents a hydrogen atom, a halogen atom, an alkyl group having 1 to 4 carbon atoms or an alkoxyl group having 1 to 4 carbon atoms, Z represents an oxygen atom or a sulfur atom, $R^1$ represents an alkyl group having 1 to 4 carbon atoms, and $R^2$ represents a halogen atom, an alkylthio group having 1 to 4 carbon atoms or an alkoxyl group having 1 to 4 carbon atoms). The present invention also relates to a process for preparing the triazine derivative represented by the general formula (I) or (II). These triazine derivatives can be prepared by the following six methods of the present invention.

Method 1

1-Benzofuranylalkylamino or 1-thianaphthenylalkylamine represented by the following general formula (III):

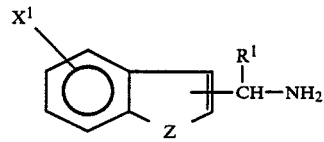

(wherein $X^1$, Z and $R^1$ are the same as defined above) is reacted with dihalogenated aminotriazine represented by the general formula (IV):

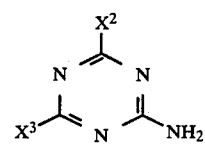

(wherein $X^2$ and $X^3$ each represent a halogen atom) to prepare a triazine derivative (halogen-containing triazine derivative) represented by the general formula (I'):

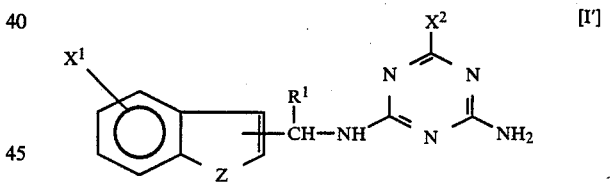

(wherein $X^1$, $X_2$, Z and $R^1$ are the same as defined above).

Method 2

1-Dihydrobenzofuranylalkylamine or 1-dihydrothianaphthenylalkylamine represented by the general formula (III'):

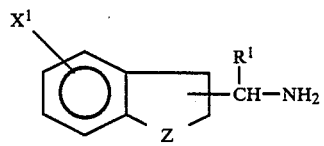

(wherein $X^1$, Z and $R^1$ are the same as defined above) is reacted with dihalogenated aminotriazine represented by the above general formula (IV) to prepare a triazine derivative (halogen-containing triazine derivative) represented by the general formula (II'):

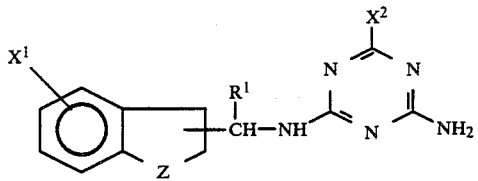

(wherein $X^1$, $X^2$, Z and $R^1$ are the same as defined above).

Method 3

A halogen-containing triazine derivative represented by the general formula (I') is reacted with alkylmercaptan represented by the general formula (V):

$$R^3SH$$

(wherein $R^3$ represents an alkyl group having 1 to 4 carbon atoms), or alkylmercaptide represented by the general formula (VI):

$$(R^3S)_nM$$

(wherein M represents an alkali metal or an alkaline earth metal, n represents the valence of M, and $R^3$ is the same as defined above) to prepare a triazine derivative (sulfur-containing triazine derivative) represented by the general formula (I''):

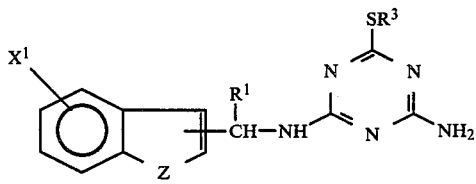

(wherein $X^1$, Z, $R^1$ and $R^3$ are the same as defined above).

Method 4

A halogen-containing triazine derivative represented by the general formula (II') is reacted with alkylmercaptan represented by the general formula (V) or alkylmercaptide represented by the general formula (VI) to prepare a triazine derivative (sulfur-containing triazine derivative) represented by the general formula (II''):

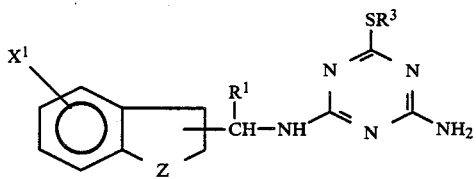

(wherein $X^1$, Z, $R^1$ and $R^3$ are the same as defined above).

Method 5

A halogen-containing triazine derivative represented by the general formula (I') is reacted with alcohol represented by the general formula (VII):

$$R^3OH$$

or alkoxide represented by the general formula (VIII):

$$(R^3O)_nM$$

(wherein $R^3$, M and n are the same as defined above) to prepare a triazine derivative (oxygen-containing triazine derivative) represented by the general formula (I'''):

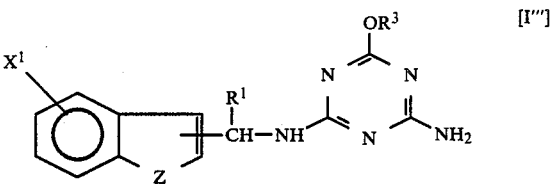

(wherein $X^1$, Z, $R^1$ and $R^3$ are the same as defined above).

Method 6

A halogen-containing triazine derivarive represented by the general formula (II') is reacted with alcohol represented by the general formula (VII) or alkoxide represented by the general formula (VIII) to prepare a triazine derivative (oxygen-containing triazine derivative) represented by the general formula (II'''):

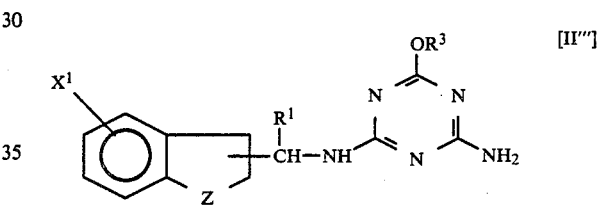

(wherein $X^1$, Z, $R^1$ and $R^3$ are the same as defined above).

The present invention further relates to a herbicide comprising (i) a herbicidal carrier, and (ii) an effective amount of a triazine derivative represented by the general formula (I) or (II).

DETAILED DESCRIPTION OF THE INVENTION

The symbols used in the general formula (I) are described below in detail.

$X^1$ represents a hydrogen atom a halogen atom, an alkyl group having 1 to 4 carbon atoms or an alkoxyl group having 1 to 4 carbon atoms.

Typical examples of the halogen atom are a chlorine atom, a bromine atom and an iodine atom. Typical examples of the alkyl group are a methyl group, an ethyl group, a propyl group, and a butyl group. Typical examples of the alkoxyl group are a methoxy group, an ethoxy group, a propoxy group and a butoxy group.

Z represents an oxygen atom or a sulfur atom.

$R^1$ represents an alkyl group having 1 to 4 carbon atoms, such as a methyl group, an ethyl group, a n-propyl group, an isopropyl group, a n-butyl group, an isobutyl group, a sec-butyl group and a tert-butyl group.

$R^2$ represents a halogen atom, an alkylthio group having 1 to 4 carbon atoms, or an alkoxyl group having 1 to 4 carbon atoms. Typical examples of the halogen atom are a chlorine atom, a bromine atom and an iodine atom. Typical examples of the alkylthio group are a methylthio group, an ethylthio group, a propylthio group, and a butylthio group. Typical examples of the alkoxyl group are a methoxy group, an ethoxy group, a propoxy group and a butoxy group.

The triazine derivatives represented by the general formula (I) can be divided into the four groups shown below depending on the type of Z and the linking position of the aminoalkyl group

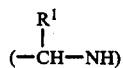

to the benzofuranyl or thianaphthenyl group.

Z=oxygen atom

Triazine derivatives (triazine derivatives containing a 2-benzofuranyl group) represented by the general formula (I-1):

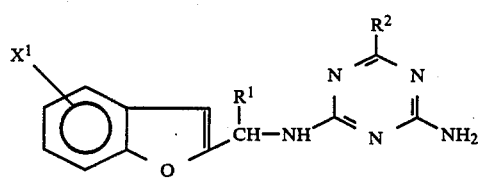

Triazine derivatives (triazine derivatives containing a 3-benzofuranyl group) represented by the general formula (I-2):

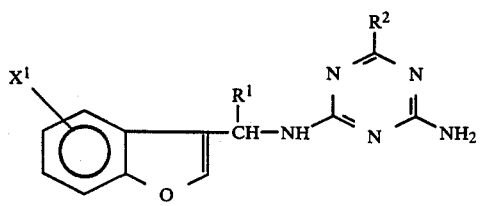

Z=sulfur atom

Triazine derivatives (triazine derivatives containing a 2-benzothiafuranyl group (2-benzothiophenyl group or 2-thianaphthenyl group)) represented by the general formula (I-3):

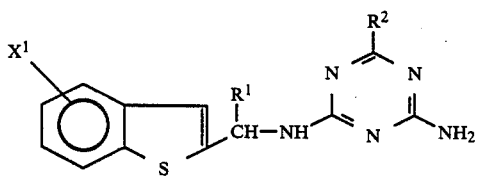

Triazine derivatives (triazine derivatives containing a 3-benzothiafuranyl group (3-benzothiophenyl group or 3-thianaphthenyl group)) represented by the general formula (I-4):

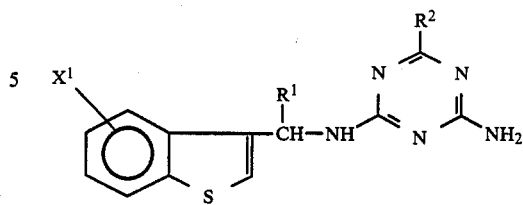

The compounds represented by the general formula (II) are also triazine derivatives (triazine derivatives containing a dihydrobenzofuranyl or dihydrobenzothiafuranyl group). The single difference between the triazine derivatives of the general formula (I) and the triazine derivatives of the general formula (II) is if or not the carbon-carbon double bond in the 2 and 3-positions of the benzofuranyl or benzothiafuranyl group is saturated. Thus, the representative examples of $X^1$, Z, $R^1$ and $R^3$ in the general formula (II) are the same as listed in the general formula (I).

The triazine derivatives represented by the general formula (II) can also be divided into the four groups shown below depending on the type of Z and the linking position of the aminoalkyl group

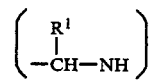

to the benzofuranyl or thianaphthenyl group as in the general formula (I).

Z=oxygen atom

Triazine derivatives (triazine derivatives containing a 2-dihydrobenzofuranyl group) represented by the general formula (II-1):

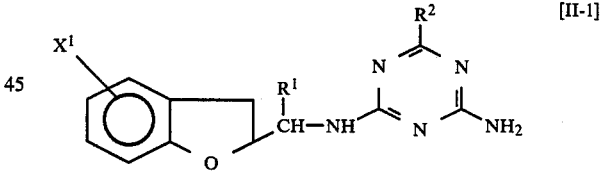

Triazine derivatives (triazine derivatives containing a 3-dihydrobenzofuranyl group, represented by the general formula (II-2):

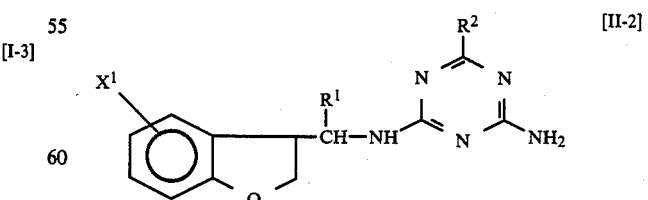

Z=sulfur atom

Triazine derivatives (triazine derivatives containing a 2-dihydrobenzothiafuranyl group (2-dihydrobenzothiophenyl group or 2-dihydrothianaphthenyl group)) represented by the general formula (II-3):

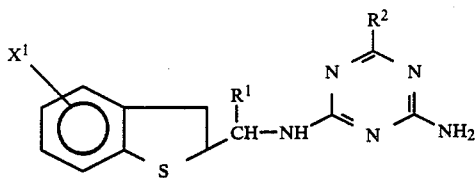

Triazine derivatives (triazine derivatives containing a 3-dihydrobenzothiafuranyl group (3-dihydrobenzothiophenyl group or 3-dihydrothianaphthenyl group)) represented by the general formula (II-4):

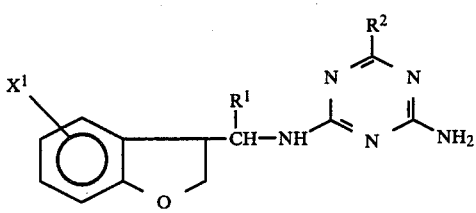

Representative examples of the triazine derivatives represented by the general formulae (I-1) to (I-4) and (II-1) to (II-4) according to the present invention are 2-chloro-4-amino-6-[1'-(2'-benzofuranyl)ethylamino)]-s-triazine; 2-bromo-4-amino-6-[1'-(2'-benzofuranyl)ethylamino]-s-triazine; 2-chloro-4-amino-6-[1'-(2'-benzofuranyl)-propylamino]-s-triazine; 2-chloro-4-amino-6-[1'-(2'-benzofuranyl)butylamino]-s-triazine; 2-methylthio-4-amino-6-[1'-(2'-benzofuranyl)ethylamino]-s-triazine; 2-ethylthio-4-amino-6-[1'-(2'-benzofuranyl)ethylamino]-s-triazine; 2-propylthio-4-amino-6-[1'-(2'-benzofuranyl)-ethylamino]-s-triazine; 2-methylthio-4-amino-6-[1'-(2'-benzofuranyl)propylamino]-s-triazine; 2-methylthio-4-amino-6-[1'-(2'-benzofuranyl)-butylamino]-s-triazine; 2-chloro-4-amino-6-[1'-(2'-(5'-chlorobenzofuranyl))ethylamino]-s-triazine; 2-chloro-4-amino-6-[1'-(3'-thianaphthenyl)ethylamino]-s-triazine; 2-chloro-4-amino-6-[1'-(2'-thianaphthenyl)ethylamino]-s-triazine; 2-chloro-4-amino-6-[1'-(2'-(2',3'-dihydrobenzofuranyl)ethylamino]-s-triazine; 2-methylthio-4-amino-6-[1'-(2'-(5'-chlorobenzofuranyl))ethylamin]-s-triazine; 2-methylthio-4-amino-6-[1'-(3'-thianaphthenyl)ethylamino]-s-triazine; 2-methylthio-4-amino-6-[1'-(2'-thianaphthenyl)ethylamino]-s-triazine; 2-methylthio-4-amino-6-[1'-(2'-(2',3'-dihydrobenzofuranyl))ethylamino]-s-triazine; 2-ethylthio-4-amino-6-[1'-(2'-thianaphthenyl)ethylamino]-s-triazine; 2-methoxy-4-amino-6-[1'-(2'-benzofuranyl)ethylamino]-s-triazine; 2-methoxy-4-amino-6-[1'-(2'-benzofuranyl)propylamino]-s-triazine; 2-methoxy-4-amino-6-[1'-(2'-thianaphthenyl)ethylamino]-s-triazine; 2-ethoxy-4-amino-6-[1'-(2'-benzofuranyl)ethylamino]-s-triazine; 2-ethoxy-4-amino-6-[1'-(2'-thianaphthenyl)ethylamino]-s-triazine; 2-chloro-4-amino-6-[1'-(2'-thianaphthenyl)propylamino]-s-triazine; 2-chloro-4-amino-6-[1'-(2'-thianaphthenyl)butylamino]-s-triazine; 2-chloro-4-amino-6-[1'-(2'-(5'-fluorobenzofuranyl)ethylamino]-s-triazine; 2-chloro-4-amino-6-[1'-(2'-(5'-chlorothianaphthenyl))ethylamino]-s-triazine; 2-chloro-4-amino-6-[1'-(2'-(7'-chlorobenzofuranyl))ethylamino]-s-triazine; 2-methylthio-4-amino-6-[1'-(2'-trianaphthenyl)propylamino]-s-triazine; 2-methylthio-4-amino-6-[1'-(2'-thianaphthenyl)butylamino]-s-triazine; 2-methylthio-4-amino-6-[1'-(2'-(5'-chlorothianaphthenyl))ethylamino]-s-triazine; 2-methylthio-4-amino-6-[1'-(2'-(5'-fluorobenzofuranyl))ethylamino]-s-triazine; 2-methylthio-4-amino-6-[1'-(2'-(7'-chlorobenzofuranyl))ethylamino]-s-triazine; 2-ethylthio-4-amino-6-[1'-(2'-(thianaphthenyl))propylamino]-s-triazine; 2-ethylthio-4-amino-6-[1'-(2'-(thianaphthenyl))butylamino]-s-triazine; 2-ethylthio-4-amino-6-[1'-(2'-(5'-chlorothianaphthenyl))ethylamino]-s-triazine; 2-ethylthio-4-amino-6-[1'-(2'-(5'-fluorobenzofuranyl))ethylamino]-s-triazine; 2-ethylthio-4-amino-6-[1'-(2'-(7'-chlorobenzofuranyl))ethylamino]-s-triazine; 2-methoxy-4-amino-6-[1'-(2'-thianaphthenyl)propylamino]-s-triazine; 2-methoxy-4-amino-6-[1'-(2'-thianaphthenyl)butylamino]-s-triazine; 2-methoxy-4-amino-6-[1'-(2'-(5'-chlorothianaphthenyl))ethylamino]-s-triazine; 2-methoxy-4-amino-6-[1'-(2'-(5'-fluorobenzofuranyl))ethylamino]-s-triazine; 2-methoxy-4-amino-6-[1'-(2'-(7'-chlorobenzofuranyl))ethylamino]-s-triazine; 2-ethoxy-4-amino-6-[1'-(2'-thianaphthenyl)propylamino]-s-triazine; 2-ethoxy-4-amino-6-[1'-(2'-thianaphthenyl)butylamino]-s-triazine; 2-ethoxy-4-amino-6-[1'-(2'-(5'-chlorothianaphthenyl))ethylamino]-s-triazine; 2-ethoxy-4-amino-6-[1'-(2'-(5'-fluorobenzofuranyl))ethylamino]-s-triazine; 2-ethoxy-4-amino-6-[1'(2'-(7'-chlorobenzofuranyl))ethylamino]-s-triazine; 2-methylthio-4-amino-6-[1'-(2'-(5'-methylbenzofuranyl))ethylamino]-s-triazine; 2-methylthio-4-amino-6-[1'-(2'-(6'-methylbenzofuranyl))ethylamino]-s-triazine; 2-methylthio-4-amino-6-[1'-(2'-7'-methylbenzofuranyl))ethylamino]-s-triazine; 2-methylthio-4-amino-6-[1'-(2'-(5'-methoxybenzofuranyl))ethylamino]-s-triazine; 2-methylthio-4-amino-6-[1'-(2'-(6'-methoxybenzofuranyl))ethylamino]-s-triazine; 2-methylthio-4-amino-6-[1'-(2'-(7'-methoxybenzofuranyl))ethylamino]-s-triazine; 2-methylthio-4-amino-6-[1'-(2'-(6'-ethylbenzofuranyl))ethylamino]-s-triazine; 2-methylthio-4-amino-6-[1'-(2'-(6'-isopropylbenzofuranyl))ethylamino]-s-triazine; 2-methylthio-4-amino-6-[1'-(2'-(6'-tert-butylbenzofuranyl))ethylamino]-s-triazine; 2-methylthio-4-amino-6-[1'-(2'(6'-ethoxybenzofuranyl))ethylamino]-s-triazine; 2-methylthio-4-amino-6-[1'-(2'-(6'-isopropoxybenzofuranyl))ethylamino]-s-triazine; 2-methylthio-4-amino-6-[1'-(2'-(6'-tert-butoxybenzofuranyl))ethylamino]-s-triazine; 2-methylthio-4-amino-6-[1'-(2'-(6'-methylbenzofuranyl))propylamino]-s-triazine; 2-methylthio-4-amino-6-[1'-(2'-(6'-isopropylbenzofuranyl))propylamino]-s-triazine; 2-ethylthio-4-amino-6-[1'-(2'-(6'-methylbenzofuranyl))ethylamino]-s-triazine; 2-methoxy-4-amino-6-[1'-(2'-(5'-methylbenzofuranyl))ethylamino]-s-triazine; 2-methoxy-4-amino-6-[1'-(2'-(6'-methylbenzofuranyl))ethylamino]-s-triazine; 2-methoxy-4-amino-6-[1'-(2'-7'-methylbenzofuranyl))ethylamino]-s-triazine; 2-methoxy-4-amino-6-[1'-(2'-(5'-methoxybenzofuranyl))ethylamino]-s-triazine; 2-methoxy-4-amino-6-[1'-(2'-(6'-methoxybenzofuranyl))ethylamino]-s-triazine; 2-methoxy-4-amino-6-[1'-(2'-(7'-methoxybenzofuranyl))ethylamino]-s-triazine; 2-methoxy-4-amino-6-[1'-(2'-(6'-ethylbenzofuranyl))ethylamino]-s-triazine; 2-methoxy-4-amino-6-[1'-(2'-(6'-isopropylbenzofuranyl))ethylamino]-s-triazine; 2-methoxy-4-amino-6-[1'-(2'-(6'-tert-butylbenzofuranyl))ethylamino]-s-triazine; 2-methoxy-4-amino-6-[1'-(2'-(6'-ethoxybenzofuranyl))ethylamino]-s-triazine; 2-methoxy-4-amino-6-[1'-(2'-(6'-isopropoxybenzofuranyl))ethylamino]-s-triazine; 2-methoxy-4-amino-6-[1'-(2'-(6'-tert-butoxybenzofuranyl))ethylamino]-s-triazine; 2-methoxy-4-amino-6-[1'-(2'-(6'-methylbenzofuranyl))propylamino]-s-triazine; 2-methoxy-4-amino-6-[1'-(2'-(6'-isopropylbenzofuranyl))- propylamino]-s-triazine; 2-ethoxy-4-amino-6-[1'-(2'-(6'-methylbenzofuranyl))ethylamino]-s-triazine; 2-chloro-4-amino-6-[1'-(2'-(5'-methylbenzofuranyl))ethylamino]-s-triazine; 2-chloro-4-amino-6-[1'-(2'-(6'-methylbenzofuranyl))ethylamino]-s-triazine; 2-chloro-4-amino-6-[1'-(2'-(7'-methylbenzofuranyl))ethylamino]-s-triazine; 2-chloro-4-amino-6-[1'-(2'-(5'-methoxybenzofuranyl))ethylamino]-s-triazine; 2-chloro-4-amino-6-[1'-(2'-(6'-methoxybenzofuranyl))ethylamino]-s-triazine; 2-chloro-4-amino-6-[1'-(2'-(7'-methoxybenzofuranyl))ethylamino]-s-triazine; 2-chloro-4-amino-6-[1'-(2'-(6'-ethylbenzofuranyl))ethylamino]-s-triazine; 2-chloro-4-amino-6-[1'-(2'-(6'-isopropylbenzofuranyl))ethylamino]-s-triazine; 2-chloro-4-amino-6-[1'-(2'-(6'-tert-butylbenzofuranyl))ethylamino]-s-triazine; 2-chloro-4-amino-6-[1'-(2'-(6'-ethoxybenzofuranyl))ethylamino]-s-triazine; 2-chloro-4-amino-6-[1'-(2'-(6'-isopropoxybenzofuranyl))ethylamino]-s-triazine; 2-chloro-4-amino-6-[1'-(2'-(6'-tert-butoxybenzofuranyl))ethylamino]-s-triazine; 2-chloro-4-amino-6-[1'-(2'-(6'-methylbenzofuranyl))propylamino]-s-triazine; 2-chloro-4-amino-6-[1'-(2'-(6'-isopropylbenzofuranyl))propylamino]-s-triazine; 2-bromo-4-amino-6-[1'-(2'-(6'-methylbenzofuranyl))ethylamino]-s-triazine.

Triazine derivatives represented by the general formula (I) can be prepared by various methods. In particular, Methods 1, 3 and 5 of the present invention as described above permit efficient preparation of the triazine derivatives.

The triazine derivatives represented by the general formula (I) of the present invention can be divided into the triazine derivatives (halogen-containing triazine derivatives) represented by the general formula (I'), the triazine derivatives (sulfur-containing triazine derivatives) represented by the general formula (I''), and triazine derivatives (oxygen-containing triazine derivatives) represented by the general formula (I''') depending on the substituent linked to the triazine ring.

The halogen-containing triazine derivatives represented by the general formula (I') can be efficiently prepared by Method 1 of the present invention. In accordance with Method 1, 1-benzofuranylalkylamine or 1-thianaphthenylalkylamine represented by the general formula (III) is reacted with dihalogenated aminotriazine represented by the general formula (IV) to form the desired halogen-containing triazine derivative of the general formula (I').

Representative examples of the 1-benzofuranylalkylamine or 1-thianaphthenylalkylamine represented by the general formula (III) are 1-(2'-benzofuranyl)ethylamine, 1-(2'-benzofuranyl)propylamine, 1-(2'-benzofuranyl)butylamine, 1-(2'-(5'-chlorobenzofuranyl))ethylamine, 1-(2'-(5'-fluorobenzofuranyl))ethylamine, 1-(2'-7'-chlorobenzofuranyl))ethylamine, 1-(2'-thianaphthenyl)ethylamine, 1-(2'-thianaphthenyl)propylamine, 1(2'-thianaphthenyl)butylamine, 1-(3'-thianaphthenyl)ethylamine, 1-(3'-thianaphthenyl)propylamine, 1-(3'-thianaphthenyl)butylamine, 1-[2'-(5'-chlorothianaphthenyl)]ethylamine, 1-]2'-(5'-chlorothianaphthenyl)]propylamine, 1-[2'-(5'-chlorothianaphthenyl)]butylamine, 1-[2'-(5'-methylbenzofuranyl)]ethylamine; 1-[2'-(6'-methylbenzofuranyl)]ethylamine; 1-[2'-(7'-methylbenzofuranyl)]ethylamine; 1[2'-(5'-methoxybenzofuranyl)]ethylamine; 1-[2'-(6'-methoxybenzofuranyl)]ethylamine; 1-[2'-(7'-methoxybenzofuranyl)]ethylamine; 1-[2'-(6'-ethylbenzofuranyl)]ethylamine; 1-[2'-(6'-isopropylbenzofuranyl)]ethylamine; 1-[2'-(6'-tert-butylbenzofuranyl)]ethylamine; 1-[2'-(6'-ethoxybenzofuranyl)]ethylamine; 1-[2'-(6'-isopropoxybenzofuranyl)]ethylamine; 1-[2'-(6'-tert-butoxybenzofuranyl)]ethylamine; 1-[2'-(6'-methylbenzofuranyl)]propylamine; 1-[2'-(6'-isopropylbenzofuranyl)]propylamine. This 1-benzofuranylalkylamine or 1-thianaphthenylalkylamine can be prepared by various methods. In accordance with one of the methods, it can be prepared as follows.

Benzofuranylalkylketone or thianaphthenylalkylketone (e.g., 2-benzofuranylmethylketone and 2-thianaphthenylmethylketone) represented by the general formula (IX):

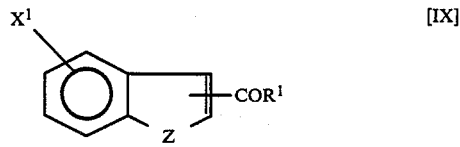

(wherein $X^1$, Z and $R^1$ are the same as defined above) is reacted with hydroxylamine, for example, to form benzofuranylalkylketoneoxime or thianaphthenylalkylketoneoxime (e.g., 2-benzofuranylmethylketoneoxime and 2-thianaphthenylmethylketoneoxime) represented by the general formula (X):

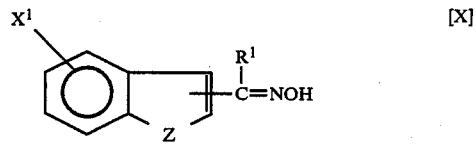

(wherein $X^1$, Z and $R^1$ are the same as defined above), and the benzofuranylalkylketoneoxime or thianaphthenylalkylketoneoxime thus formed is reduced with a reducing agent or is subjected to catalytic reduction to form the 1-benzofuranylalkylamine or 1-thianaphthenylalkylamine represented by the general formula (III).

Also, by replacing hydroxylamine with ammonium formate in the above reaction to form the corresponding formamine derivative and hydrolyzing the formamide derivative with concentrated hydrochloric acid or caustic alkali, the 1-benzofuranylalkylamine or 1-thianaphthenylalkylamine can be obtained.

The dihalogenated aminotriazine represented by the general formula (IV), that is, 2,6-dihalogeno-4-amino-s-triazine includes 2,6-dichloro-4-amino-s-triazine. This dihalogenated aminotriazine can be obtained by reacting cyanuric halide, such as cyanuric chloride, with ammonia.

In accordance with Method 1 of the present invention, as described above, the 1-benzofuranylalkylamine or 1-thianaphthenylalkylamine represented by the general formula (III) is reacted with the dihalogenated aminotriazine represented by the general formula (IV). In this reaction, the compounds are used in an equimolar amount, and a solvent is not always needed. Solvents which can be used include ketones such as acetone, methyl ethyl ketone, and cyclohexanone, aliphatic hydrocarbons such as n-hexane, and n-heptane, cyclic hydrocarbons such as benzene, decalin and alkylnaphthalene, chlorinated hydrocarbons such as carbon tetrachloride and ethylene tetrachloride, and ethers such as tetrahydrofuran and dioxane. It is effective to add a deacidification agent (dehydrohalogenation agent) such as sodium hydrogencarbonate and triethylamine to the reaction system. The reaction temperature is not critical; the reaction proceeds satisfactorily at various temperatures from high temperatures to low temperatures, more specifically 10° to 100° C.

In accordance with Method 1 of the present invention, the halogen-containing triazine derivative represented by the general formula (I') is prepared in high purity and high yield.

In accordance with Method 3 of the present invention, the halogen-containing triazine derivative represented by the general formula (I') is first prepared by Method 1 of the present invention, and then the above triazine derivative is reacted with alkylmercaptan represented by the general formula (V) or alkylmercaptide represented by the general formula (VI) to form the desired sulfur-containing triazine derivative represented by the general formula (I'').

Examples of the alkylmercaptan are methylmercaptan, ethylmercaptan and propylmercaptan. Examples of the alkylmercaptide are sodium methylmercaptide ($CH_3SNa$), potassium methylmercaptide ($CH_3SK$), magnesium methylmercaptide (($CH_3S)_2Mg$), sodium ethylmercaptide ($C_2H_5SNa$), potassium ethylmercaptide ($C_2H_5SK$) and magnesium ethylmercaptide (($C_2H_5S)_2Mg$). In a case where alkylmercaptan is used in Method 3, it is preferred that the reaction be carried out in the presence of caustic alkali, such as sodium hydroxide and potassium hydroxide.

In Method 3 of the present invention, the mixing ratio of the halogen-containing triazine derivative represented by the general formula (I') and the alkylmercaptan or alkylmercaptide is not critical; usually they are used in such an amount that the molar ratio of the halogen-containing triazine derivative of the general formula (I') and the alkylmercaptan or alkylmercaptide is nearly equal. This reaction can be carried out in the absence or the presence of a solvent, such as isopropyl alcohol, dimethylformamide, toluene, xylene, acetone and benzene. The reaction temperature is not critical; the reaction proceeds satisfactorily at various temperatures from high temperatures to low temperatures, more specifically 10° to 150° C.

After the reaction is completed, the reaction mixture is cooled, and the solid material thus obtained is washed and further purified by chromatography using a silica gel column, whereupon the sulfur-containing triazine derivative represented by the general formula (I'') is obtained in high purity and high yield.

In accordance with Method 5 of the present invention, the halogen-containing triazine derivative represented by the general formula (I') is first prepared by Method 1 of the present invention, and then the halogen-containing triazine derivative thus obtained is reacted with the alcohol represented by the general formula (VII) or alkoxide represented by the general formula (VIII) to form the desired oxygen-containing triazine derivative represented by the general formula (I''').

Examples of the alcohol are methyl alcohol, ethyl alcohol and propyl alcohol. Examples of the alkoxide are sodium methoxide ($CH_3ONa$), potassium methoxide ($CH_3OK$), calcium methoxide (($CH_3O)_2Ca$), sodium ethoxide ($C_2H_5ONa$), potassium ethoxide ($C_2H_5OK$), and calcium ethoxide (($C_2H_5O)_2Ca$). In a case where alcohol is used in Method 5, it is preferred that the reaction be carried out in the presence of alkali metal, such as metallic sodium and metallic potassium.

In Method 5 of the present invention, the mixing ratio of the halogen-containing triazine derivative of the general formula (I') and the alcohol or alkoxide is not critical; usually they are used in such an amount that the molar ratio of the halogen-containing triazine derivative of the general formula (I') to the alcohol or alkoxide is nearly equal. The reaction can be carried out in the absence or the presence of a solvent. Preferred examples of solvents which can be used are alcohols such as methyl alcohol, ethyl alcohol and isopropyl alcohol. The reaction temperature is not critical; the reaction proceeds satisfactorily at various temperatures from high temperatures to low temperatures, more specifically 10° to 110° C.

After the reaction is completed, the reaction mixture is cooled, and the solid material thus obtained is washed, purified by chromatography using a silica gel column, and dried, whereupon the oxygen-containing triazine derivative represented by the general formula (I''') can be obtained in high purity and high yield.

The triazine derivative (triazine derivative containing a dihydrobenzofuranyl or dihydrobenzothiafuranyl group) represented by the general formula (II) can also be prepared by various methods as in the preparation of the triazine derivative of the general formula (I). In particular, Methods 2, 4 and 6 of the present invention as described above permit efficient preparation of the triazine derivatives.

The triazine derivatives represented by the general formula (II) of the present invention can be divided into the triazine derivative (halogen-containing triazine derivative) represented by the general formula (II'), the triazine derivative (sulfur-containing triazine derivative) represented by the general formula (II'') and the triazine derivative (oxygen-containing triazine derivative) represented by the general formula (II''') depending on the type of the substituent linked to the triazine ring.

The halogen-containing triazine derivative represented by the general formula (II') can be prepared efficiently by Method 2 of the present invention. In accordance with Method 2 of the present invention, the 1-dihydrobenzofuranylalkylamine or 1-dihydrothianaphthenylalkylamine represented by the general formula (III') is reacted with the dihalogenated aminotriazine represented by the general formula (IV) to form the desired halogen-containing triazine derivative represented by the general formula (II').

Examples of the 1-dihydrobenzofuranylalkylamine or 1-dihydrothianaphthenylalkylamine represented by the general formula (III') are 1-[2'-(2',3'-dihydrobenzofuranyl)]ethylamine, 1-[2'-(2',3'-dihydrobenzofuranyl)]propylamine, 1-[2'-(2',3'-dihydrobenzofuranyl)]butylamine, 1-[2'-(2',3'-dihydrothianaphthenyl)]ethylamine, 1-[2'-(2',3'-dihydrothianaphthenyl)]propylamine, 1-[2'-(2',3'-dihydrothianaphthenyl)]butylamine, 1-[3'-(2',3'-dihydrothianaphthenyl)]ethylamine, 1-[3'-(2',3'-dihydrothianaphthenyl)]propylamine, 1-[3'-(2',3'-dihydrothianaphthenyl)]butylamine, 1-[2'-(5'-chloro-(2',3'-dihydrobenzofuranyl))]ethylamine, 1-[2'-(5'-fluoro-(2',3'-dihydrobenzofuranyl))]ethylamine, 1-[2'-(7'-chloro-(2',3'-dihydrobenzofuranyl))]ethylamine, 1-[2'-(5'-methyl-(2',3'-dihydrobenzofuranyl))]ethylamine, 1-[2'-(6'-methyl-(2',3'-dihydrobenzofuranyl))]ethylamine, 1-[2'-(7'-methyl-(2',3'-dihydrobenzofuranyl))]ethylamine, 1-[2'-(5'-methoxy-(2',3'-dihydrobenzofuranyl))]ethylamine, 1-[2'-(6'-methoxy-(2',3'-dihydrobenzofuranyl))]ethylamine, 1-[2'-(7'-methoxy-(2',3'-dihydrobenzofuranyl))]ethylamine, 1-[2'-(6'-ethyl-(2',3'-dihydrobenzofuranyl))]ethylamine, 1-[2'-(6'-isopropyl-(2',3'-dihydrobenzofuranyl))]ethylamine, 1-[2'-(6'-tert-butyl-(2',3'-dihydrobenzofuranyl))]ethylamine, 1-[2'-(6'-ethoxy-(2',3'-dihydrobenzofuranyl))]ethylamine, 1-[2'-(6'-tert-butoxy-(2',3'-dihydrobenzofuranyl))]ethylamine, 1-[2'-(6'-methyl-(2',3'-dihydrobenzofuranyl))]propylamine, 1-[2'-(6'-isopropyl-(2',3'-dihydrobenzofuranyl))]propylamine.

In preparing the above 1-dihydrobenzofuranylalkylamine or 1-dihydrothianaphthenylalkylamine, various methods may be employed. An example of these methods is a method of catalytically reducing the 1-benzofuranylalkylamine or 1-thianaphthenylalkylamine represented by the general formula (III) as described above.

Method 2 of the present invention can be carried out in the same manner as in Method 1 as described above except that the 1-dihydrobenzofuranylalkylamine or 1-dihydrothianaphthenylalkylamine of the general formula (III') is used in place of the 1-benzofuranylalkylamine or 1-thianaphthenylalkylamine of the general formula (III).

In accordance with Method 2, the halogen-containing triazine derivative represented by the general formula (II') can be obtained in high purity and high yield.

In accordance with Method 4 of the present invention, the halogen-containing triazine derivatives represented by the general formula (II') is prepared according to Method 2 of the present invention as described above, and thereafter the triazine derivative of the general formula (II') is reacted with the alkylmercaptan represented by the general formula (V) or the alkylmercaptide represented by the general formula (VI) to form the desired sulfur-containing triazine derivative represented by the general formula (III').

Method 4 can be carried out in the same manner as in Method 3 as described above.

In accordance with Method 6 of the present invention, the halogen-containing triazine derivative represented by the general formula (II') is prepared according to Method 2 of the present invention as described above and, thereafter, the triazine derivative of the general formula (II') is reacted with the alcohol represented by the general formula (VII) or the alkoxide represented by the general formula (VIII) to form the desired oxygen-containing triazine derivative represented by the general formula (II''').

Method 6 can be carried out in the same manner as in Method 5 as described above.

The halogen-containing triazine derivative represented by the general formula (I') which is prepared by Method 1 of the present invention, the sulfur-containing triazine derivative represented by the general formula (I'') which is prepared by Method 3 of the present invention, and the oxygen-containing triazine derivative represented by the general formula (I''') which is prepared by Method 5 of the present invention are all included in the triazine derivative represented by the general formula (I) of the present invention and are all novel compounds.

The halogen-containing triazine represented by the general formula (II') which is prepared by Method 2 of the present invention, the sulfur-containing triazine deirvative represented by the general formula (II'') which is prepared by Method 4 of the present invention, and the oxygen-containing triazine derivative represented by the general formula (I''') which is prepared by Method 6 of the present invention are all included in the triazine derivative represented by the general formula (II) of the present invention and are all novel compounds.

The triazine derivative represented by the general formula (I) or (II) inhibits the germinating and growth of weeds and further exhibits high selectivity and, therefore, is suitable for use as a herbicide. Moreover the triazine derivatives are excellent herbicidal activity against annual broadleaf weeds such as *Rotala indica*(-Willd.)Koehne var. *uligirosa*(Miq.)Koehne, *Lindernia pyxidaria* L. and *Monochoria vaginalis* Presl var. *plantaginea*(Roxb.)Solms-Laub., species of Cyperaceae such as *Cyperus difformis* L., and Graminceae such as *Echinochloa crus-galli* L., as well as perennial weeds such as *Scirpus juncoides* Roxb. var. Hotarui Ohwi, *Cyperus serotinus* Rottb. and *Sagittaria pygmaea* Miq. which are now considered to be difficult to control, without causing phytotoxicity to paddy rice plants.

The triazine derivative represented by the general formula (I) or (II) exhibits an excellent herbicidal activity against troublesome weeds such as sicklepod (Cassia obtusifolia L), tallmorning glory (Ipomea purpurea (L) Roth) and velvet leaf (Abutilon theophrasti Medik) without injuring corns, grain sorghums, wheat, barley and oats.

Herbicides of the present invention comprises (i) a herbicidal carrier, and (ii) an effective amount of the triazine derivative of the general formula (I) or (II).

The herbicides of the present invention can be applied in the form of compositions such as a wettable powder, an emulsifiable concentrate, dust, granule and the like. Such compositions are prepared by mixing the triazine derivative of the general formula (I) or (II) as the effective component with a liquid carrier such as an organic solvent and the like or a solid carrier such as a mineral powder and the like. Addition of a surfactant is preferred to impart the properties of ready emulsifying, dispersing, spreading and the like to the preparations.

When the herbicides of this invention are applied in the form of wettable powder, the herbicides usually comprise 10–55 parts by weight of the triazine derivative as the effective component, 40–88 parts by weight of a solid carrier and 2–5 parts by weight of a surfactant. When the herbicides are applied in the form of emulsifiable concentrate, the herbicides usually comprise 20–50 parts by weight of the triazine derivative as the effective component, 35–75 parts by weight of a solvent and 5–15 parts by weight of a surfactant.

When the herbicides are applied in the form of dust, the herbicides usually comprise 1–15 parts by weight of the triazine derivative as the effective component, 80–97 parts by weight of a solid carrier and 2–5 parts by weight of a surfactant. When the herbicides are applied in the form of granule, the herbicides usually comprise 0.2–15 parts by weight of the triazine derivative as the effective component, 80–97.8 parts by weight of a solid carrier and 2–5 parts by weight of a surfactant.

A mineral powder can be used as the solid carrier described above. The mineral powder includes oxide such as diatomaceous earth and slaked lime, phosphate such as apatite, sulfate such as gypsum, and silicate such as talc, pyrophyllite, clay, kaolin, bentonite, acid clay, white carbon, quartz powder and silica powder.

An organic solvent can be used as the solvent described above. The organic solvent includes an aromatic hydrocarbon such as xylene, toluene and benzene, a chlorinated hydrocarbon such as o-chlorotoluene, trichloromethane and trichloroethylene, an alcohol such as cyclohexanol, amylalcohol and ethylene glycol, a ketone such as isophorone, cyclohexanone and cyclohexenylcyclohexanone, an ether such as butylcellosolve, dimethylether and methylethylether, an ester such as isopropyl acetate, benzyl acetate and methyl phthalate, an amide such as dimethylformamide, and a mixture thereof. The above surfactant includes various kinds of surfactant, that is anion type, cation type, non-ion type and amphoteric ion type (e.g. amino acid and betaine).

The novel triazine derivatives of the general formula (I) or (II) of the present invention, which are a novel compound, is high weed control activity against annual weeds as well as perennial weeds and exhibits high selectivity and thus is useful as a herbicide not causing any injury against paddy rice plants. Furthermore, when the triazine derivative of the general formula (I) or (II) is used as a foliage-applied herbicide for upland field crops such as corn, wheat, barley, oats and grain sorghum, it is more effective than the conventional foliage-applied herbicide for upland field crops.

In the herbicide of the present invention, as the effective component, other herbicidal materials can be used in combination with the triazine derivative of the general formula (I) or (II). These other herbicidal materials include conventionally used herbicides. Examples of such conventionally used herbicides are a pheoxy-based herbicide, a diphenyl ether-based herbicide, a triazine-based herbicide, a urea-based herbicide, a carbamate-based herbicide, a thiol carbamate-based herbicide, an acid anilide-based herbicide, a pyrazole-based herbicide, phosphoric acid-based herbicide, a sulfonylurea-based herbicide, and an oxadiazone-based herbicide.

If desired, the herbicide of the present invention can be used in admixture with an insecticide, a germicide, a plant growth-regulator, a fertilizer and so forth.

As described above, the triazine derivative of the present invention is a novel compound and can be used effectively as a herbicide. In accordance with Methods 1 to 6 of the present invention, the triazine derivative of the general formula (I) or (II) can be prepared in high purity and high yield. The herbicide of the present invention, containing the triazine derivative of the general formula (I) or (II) as an effective component is more effective and less damages plants than the conventional herbicides for rice plants and furthermore has a feature that the herbicidal spectral width is broad. In more detail, the herbicide of the present invention is excellent herbicidal activity against *Echinochloa crusgalli* L. and annual broadleaf weeds, as well as in killing perennial weeds such as *Sagittaria pygmaea* Miq., *Scirpus juncoides* Roxb. var. Hotarui Ohwi and *Cyperus serotinus* Rottb.

Furthermore, even when the herbicide of the present invention is used as a herbicide for upland crops, it is more effective against weeds and more selective against crops than the conventional farm herbicides. More specifically the herbicide of the present invention can be used safely in cultivation of corn and grain sorghum, and further is greatly effective against troublesome weeds such as sicklepod, tallmorning glory and velvetleaf.

The present invention is described in greater detail with reference to the following examples.

REFERENCE EXAMPLE 1

(1) Preparation of 2-Benzofuranylmethylketone oxime

Twenty six grams (g) (162 millimoles (mmol)) of commercially available 2-benzofuranylmethylketone was dissolved in 300 milliliters (ml) of methanol, and 16.9 g (243 mmol) of hydroxylamine hydrochloride and 20.4 g (243 mmol) of sodium hydrogencarbonate were added thereto. The resulting mixture was stirred at room temperature for 8 hours. Then, $\phi$ml of water was added and the methanol was distilled away under reduced pressure. Precipitated crystals were filtered off and washed with water to yield 27.8 g of 2-benzofuranylmethylketone oxime having the following formula (yield, 98%).

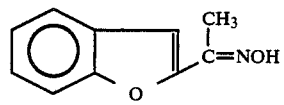

(2) Preparation of 1-(2'-Benzofuranyl)ethylamine

In a nitrogen atmosphere, 7.0 g (185 mmol) of sodium borohydride was suspended in 200 ml of diethylene glycol dimethyl ether, and 27 g (154 mmol) of 2-benzofuranylmethylketone oxime as prepared in (1) above was added thereto in a solid form while cooling with ice and stirring. In addition, a solution of 26.2 g (185 mmol) of a boron trifluorideethyl ether complex in 100 ml of diethylene glycol dimethyl ether was dropped thereto and stirred at 120° C. for 2 hours. The reaction mixture was added to 1,000 ml of ice water, made alkaline with an aqueous sodium hydroxide solution, and then extracted with ethyl ether. The ethyl ether layer was washed with water and dried over anhydrous sodium sulfate, and then the ethyl ether was distilled away under reduced pressure to yield a crude product. This crude product was subjected to vacuum distillation (b.p., 106°–110° C./3 mmHg) to obtain 1-(2'-benzofuranyl)ethylamine (yield, 29%).

The results of the elemental analysis of 1-(2'-benzofuranyl)ethylamine, and its structural formula are shown below.

Elemental Analysis (%)

|            | C    | H   | N   |
|------------|------|-----|-----|
| Found      | 74.0 | 6.9 | 8.7 |
| Calculated | 74.5 | 6.9 | 8.7 |

Structural Formula

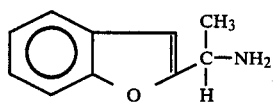

REFERENCE EXAMPLE 2

The procedure of Reference Example 1 was repeated wherein 2-benzofuranylethyl ketone was used in place of 2-benzofuranylmethyl ketone. The results are shown in Table 1.

REFERENCE EXAMPLE 3

The procedure of Reference Example 1 was repeated wherein 2-(5'-chlorobenzofuranyl)methyl ketone was used in place of 2-benzofuranylmethyl ketone. The results are shown in Table 1.

REFERENCE EXAMPLE 4

The procedure of Reference Example 1 was repeated wherein 3-thianaphthenylmethyl ketone was used in place of 2-benzofuranylmethyl ketone. The results are shown in Table 1.

Example 1, and 60 ml of acetic acid and 3.0 g of 5% palladium carbon were added thereto. The resulting mixture was stirred in a hydrogen atmosphere at room temperature for 6 days. The reaction mixture was filtered to remove insoluble substances, and 50 ml of water was added to the resulting filtrate and the methanol was distilled away under reduced pressure.

The solution was made alkaline with an aqueous sodium hydroxide solution and extracted with ethyl ether. The ethyl ether layer was washed with water and dried with anhydrous sodium sulfate, and then the ethyl ether was distilled away under reduced pressure to yield 2.1 g

TABLE I

| No. | Ketone oxime Name | Amount (Yield) | Alkylamine Name | Amount (Yield) | Structure |
|---|---|---|---|---|---|
| Reference Example 2 | 2-benzofuranyl-ethylketone oxime | 26.7 g (87%) | 1-(2'-benzofuranyl)-propylamine | 2.66 g (16%) | structure with $C_2H_5$, $CH-NH_2$ |
| Reference Example 3 | 2-(5'-chlorobenzofuranyl)-methylketone oxime | 35.7 g (98%) | 1-[2-(5'-chloro-benzofuranyl)]ethylamine | 9.39 g (33%) | structure with Cl, $CH_3$, $CH-NH_2$ |
| Reference Example 4 | 3-thianaphthenyl-methylketone oxime | 30.7 g (99%) | 1-(3-thianaphthenyl)-ethylamine | 19.0 g (67%) | structure with $CH_3$, $CH-NH_2$, S |

REFERENCE EXAMPLE 5

Preparation of 1-(2'-thianaphthenyl)ethylamine

A mixture of 12.5 g (70.9 mmol) of 2-thianaphthenyl methyl ketone and 14.3 g (227 mmol) of ammonium formate was stirred at 180° C. for 5 hours.

The reaction mixture thus obtained was dissolved in 50 ml of benzene, washed with water and dried over anhydrous sodium sulfate, and then the benzene was distilled away under reduced pressure. To the product obtained after benzene distillation was added 25 ml of 35% hydrochloric acid, and the resulting mixture was heat refluxed for 1.5 hours. After the reaction mixture was cooled, 50 ml of ethyl acetate was added, and an aqueous layer was separated. This aqueous layer was made alkaline with an aqueous sodium hydroxide solution, and an isolated oil layer was extracted with 50 ml of ethyl ether. The ethyl ether layer thus obtained was washed with water and dried over anhydrous sodium sulfate, and then the ethyl ether was distilled away to yield 5.2 g of 1-(2'-thianaphthenyl)ethylamine having the following formula (yield, 41%).

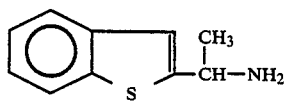

REFERENCE EXAMPLE 6

Preparation of 1-[2'-(2',3'-dihydrobenzofuranyl)]ethylamine

In 15 ml of methanol was dissolved 3.0 g (18.6 mmol) of 1-(2'-benzofuranyl)ethylamine prepared in Reference Example 1, and 60 ml of acetic acid and 3.0 g of 5% palladium carbon were added thereto.

of 1-[2'-(2',3'-dihydrobenzofuranyl)]ethylamine having the following formula (yield, 69%).

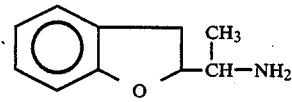

REFERENCE EXAMPLE 7

(1) Preparation of 2-(6'-methylbenzofuranyl)methylketone oxime

The procedure of Reference Example 1 (1) was repeated wherein 2-(6'-methylbenzofuranyl)methyl ketone was used in place of 2-benzofuranylmethyl ketone, thereby preparing 29.1 g of 2-(6'-methylbenzofuranyl)-methylketone oxime having the following formula (yield, 95%).

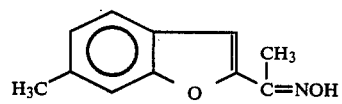

(2) Preparation of 1-[2'-(6'-methylbenzofuranyl)]ethylamine

In 250 ml of ethanol was dissolved 29.1 g (154 mmol) of 2-(6'-methylbenzofuranyl)methylketone oxime as prepared in (1) above, and 60.3 g (920 mmol) of zinc powder and 160 ml of water were added thereto. In addition, 147 g of 50% acetic acid was slowly added dropwise thereto. After addition, the resulting mixture was stirred for two hours, and filtered to remove the zinc powder, and the resulting filtrate was concentrated under reduced pressure.

The concentrate was made alkaline with an aqueous sodium hydroxide solution and extracted with ethyl ether. The ethyl ether layer was washed with water and dried with anhydrous sodium sulfate, and then the ethyl ether was distilled away under reduced pressure to yield 24.8 g of 1-[2'-(6'-methylbenzofuranyl)]ethylamine having the following formula (yield, 92%).

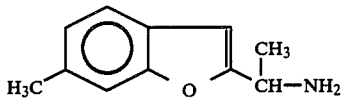

REFERENCE EXAMPLE 8

Preparation of 1-[2'-(6'-methoxybenzofuranyl)]ethylamine

In 275 ml of methanol was dissolved 20.0 g (105 mmol) of 2-(6'-methoxybenzofuranyl)methyl ketone, and 66.4 g (105 mmol) of ammonium acetate and 4.65 g (74 mmol) of cyano sodium borohydride were added thereto. The resulting mixture was stirred at room temperature for 30 hours. The reaction mixture was concentrated under reduced pressure. The concentrate was made acid with a small amount of concentrated hydrochloric acid, and then ethyl ether and water were added to separate the resulting aqueous layer. This aqueous layer was made alkaline with an aqueous sodium hydroxide solution, and was extracted with ethyl ether. The ethyl ether layer was washed with water and dried with anhydrous sodium sulfate, and then the ethyl ether was distilled away under reduced pressure to yield 15.6 g of -[2'-(6'-methoxybenzofuranyl)]ethylamine having the following formula (yield, 77%).

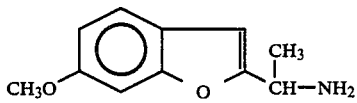

PREPARATION EXAMPLE 1

In 55 g of acetone was dissolved in 16.4 g (100 mmol) of 2,6-dichloro-4-amino-s-triazine, and 16.1 g (100 mmol) of 1-(2'-benzofuranyl)ethylamine as obtained in Reference Example 1 was added thereto. Subsequently a suspension of 8.4 g (100 mmol) of sodium hydrogencarbonate in 60 g of water was added to the above solution while stirring at 0°–5° C. Then the resulting mixture was gradually heated to 50° C. over 1 hour.

After heating, the mixture was cooled to yield a product. This product was separated, washed with water and then recrystallized from an ethanol/water mixture to obtain 27.5 g of white crystals of 2-chloro-4-amino-6-(1'-(2'-benzofuranyl)ethylamino)-s-triazine (Compound 1) (yield, 95%).

The structural formula and the analytical results of the above compound are shown in Tables 2–4.

PREPARATION EXAMPLE 2

In 5.5 g of acetone was dissolved 1.64 g (10 mmol) of 2,6-dichloro-4-amino-s-triazine, and 1.75 g (10 mmol) of 1-(2'-benzofuranyl)propylamine as obtained in Reference Example 2 was added thereto. Subsequently a suspension of 0.84 g (10 mmol) of sodium hydrogencarbonate in 6.0 g of water was added while stirring at 0°–5° C. Then the mixture was gradually heated to 50° C. over 1 hour.

Then the mixture was cooled, and the reaction product was separated, washed with water and then recrystallized from an ethanol/water mixture to yield 2.88 g of white crystals of 2-chloro-b 4-amino-6-(1'-(2'-benzofuranyl)propylamino)-s-triazine (Compound 2) (yield, 95% ). The structural formula and the analytical results of the compound as obtained above are shown in Tables 2 to 4.

PREPARATION EXAMPLES 3 TO 6 AND 20, 21

The procedure of Preparation Example 2 was repeated wherein the alkylamines prepared in Reference Examples 3 to 8 were each used in place of 1-(2'-benzofuranyl)propylamine, thereby preparing the corresponding 2-chloro-4-amino-6-alkylamino-s-triazines (Compounds 3, 4, 5, 6, 20 and 21). The structural formula and the analytical results of each of the compounds as obtained above are shown in Tables 2 to 4.

PREPARATION EXAMPLE 7

To a mixture of 90 g of isopropanol and 60 g of sodium methylcaptide having a concentration of 15% which had been heated to 50°–60° C. was added 29.0 g (100 mmol) of 2-chloro-4-amino-6-(1'-(2-benzofuranyl)ethylamino)-s-triazine as prepared in Preparation Example 1 while stirring. The resulting reaction mixture was heated under reflux for 3 hours while stirring. After the reaction mixture was cooled to 10° C., 1,000 ml of water was added thereto. The resulting mixture was extracted three times with 200 ml of ethyl acetate. The ethyl acetate layer was drived over anhydrous sodium sulfate and then the solvent was distilled away under reduced pressure. The residue was purified by developing it by silica gel column chromatography (developing solvent, toluene/ethyl acetate=8/2) to obtain 27.1 g of 2-methylthio-4-amino-6-(1'-(2'-benzofuranyl)ethylamino)-s-triazine in a colorless solid form (Compound 7) (yield, 90%).

The compound as obtained above was recrystallized from a dioxane/water mixture to obtain white crystals. The structural formula and the analytical results of the compound are shown in Tables 2 to 4.

PREPARATION EXAMPLE 8

To a mixture of 9.0 g of isopropanol and 6.0 g of sodium methylmercaptide having a concentration of 15% which had been heated to 50°–60° C. was added 2.90 g (10 mmol) of 2-chloro-4-amino-6-(1'-(2'-benzofuranyl)propylamino)-s-triazine as prepared in Preparation Example 1 while stirring. The reaction mixture thus obtained was heated under reflux for 3 hours while stirring. After the mixture was cooled to 10° C., 100 ml of water was added thereto. The resulting mixture was extracted three times with 20 ml of ethyl acetate. The ethyl acetate layer was dried over anhydrous sodium sulfate, and the solvent was distilled away under reduced pressure. The residue was purified by developing it by silica gel column chromatography (developing solvent: toluene/ethyl acetate=8/2) to obtain 2.87 g of 2-methylthio-4-amino-6-(1'-(2'-benzofuranyl)propylamino)-s-triazine in a colorless resinoid form (Compound 8) (yield, 91%). The structural formula and the analytical results of the compound are shown in Tables 2 to 4.

PREPARATION EXAMPLES 9 TO 12 AND 22, 23

The procedure of Preparation Example 8 was repeated wherein Compounds 3 to 6 as prepared in Preparation Examples 3 to 6 and 20, 21 were each used in place of 2-chloro-4-amino-6-(1'-(2'-benzofuranyl)-propylamino)-s-triazine, thereby preparing the corresponding 2-methylthio-4-amino-6-alkylamino-s-triazines (Compounds 9, 10, 11, 12, 22 and 23. The structural formula and the results of elemental analysis of each of the compounds as obtained above are shown in Tables 2 to 4.

PREPARATION EXAMPLE 13

A mixture of 0.78 g (12.5 mmol) of ehtyl mercaptan, 0.5 g (12.5 mmol) of sodium hydroxide, 6 ml of water and 15 ml of isopropyl alcohol was heated to 50°–60° C., and then 2.89 g (10 mmol) of 2-chloro-4-amino-6-(1'-(2'-benzofuranyl)ethylamino)-s-triazine (Compound 1) as prepared in Preparation Example 1 was added thereto with stirring. The resulting reaction mixture was heated under reflux with stirring for 3 hours and then cooled to 10° C. Then 100 ml of water was added. The resulting mixture was extracted three times with 20 ml of ethyl acetate. The ethyl acetate layer was dried over anhydrous sodium sulfate, and then the solvent was distilled away under reduced pressure. The residue was purified by developing it by silica gel column chromatography (developing solvent: toluene/ethyl acetate=8/2) and further recrystallized from toluene to obtain 2.93 g of 2-ethylthio-4-amino-6-(1'-(2'benzofuranyl)ethylamino)-s-triazine in a white crystal form (Compound 13) (yield, 93%). The structural formula and the analytical results of the compound as obtained above are shown in Tables 2 to 4.

PREPARATION EXAMPLE 14

The procedure of Preparation Example 13 was repeated wherein 2-chloro-4-amino-6-(1'-(2'-thianaphthenyl)ethylamino)-s-triazine (Compound 5) as prepared in Preparation Example 5 was used in place of 2-chloro-4-amino-6-(1'-(2'-benzofuranyl)ethylamino)-s-triazine, thereby preparing 2-ethylthio-4-amino-6-(1'-(2'-thianaphthenyl)ethylamino)-s-triazine (Compound 14). The structural formula and the analytical results of the compound as obtained above are shown in Tables 2 to 4.

PREPARATION EXAMPLE 15

In 20 ml of methanol was dissolved 2.90 g (10 mmol) of 2-chloro-4-amino-6-(1'-(2'-benzofuranyl)ethylamino)-s-triazine (Compound 1) as prepared in Preparation Example 1, and then 2.31 g (12 mmol) of 28% sodium methylate was added thereto. The resulting mixture was heated under reflux with stirring for 14 hours. After the methanol was distilled away under reduced pressure, the residue was dissolved in 50 ml of chloroform and washed with water. The chloroform layer was dried over anhydrous sodium sulfate, and then the solvent was distilled away under reduced pressure. The residue was purified by developing it by silica gel column chromatography (developing solvent,: toluene/ethyl acetate=8/2), thereby obtaining 2.62 g of 2-methoxy-4-amino-6-(1'-(2'-benzofuranyl)ethylamino)-s-triazine in a colorless resinoid form (Compound 15). The structural formula and the analytical results of the compound as obtained above are shown in Tables 2 to 4.

PREPARATION EXAMPLES 16 AND 17

The procedure of Preparation Example 15 was repeated wherein Compound 2 as prepared in Preparation Example 2 or Compound 5 as prepared in Preparation Example 5 was used in place of 2-chloro-4-amino-6-(1'-(2'-benzofuranyl)ethylamino)-s-triazine, thereby obtaining respectively 2-methoxy-4-amino-6-(1'-(2'-benzofuranyl)propylamino)-s-triazine (Compound 16) or 2-methoxy-4-amino-6-(1'-(2'-thianaphthenyl)ethylamino)-s-triazine Compound 17). Thereafter, Compound 17 was treated in the same manner as in Preparation Example 15, and then recrystallized from an ethanol/water mixture to obtain in a white crystal form. The structural formula and the analytical results of each compound are shown in Tables 2 to 4.

PREPARATION EXAMPLE 18

In 20 ml of ethanol was dissolved 2.90 g (10 mmol) of 2-chloro-4-amino-6-(1'-(2'-benzofuranyl)ethylamino-s-triazine (Compound 1) as prepared in Preparation Example 1, and then 0.82 g (12 mmol) of sodium ethylate was added thereto. The resulting mixture was heated under reflux with stirring for 14 hours. After the ethanol was distilled away under reduced pressure, the residue was dissolved in 50 ml of chloroform and then washed with water. The chloroform layer was drived over anhydrous sodium sulfate, and then the solvent was distilled away under reduced pressure. The residue was purified by developing it by silica gel column chromatography (developing solvent: toluene/ethyl acetate=8/2) and further recrystallized from an ethanol/water mixture to obtain 2.75 g of 2-ethoxy-4-amino-6-(1'-(2'-benzofuranyl)ethylamino)-s-triazine (Compound 18) in a white crystal form (yield, 92%). The structural formula and the analytical results of the compound as obtained above are shown in Tables 2 to 4.

PREPARATION EXAMPLE 19

The procedure of Preparation Example 18 was repeated wherein 2-chloro-4-amino-6-(1'-(2'-thianaphthenyl)ethylamino)-s-triazine (Compound 5) as prepared in Preparation Example 5 was used in place of 2-chloro-4-amino-6-(1'-(2'-benzofuranyl)ethylamino)-s-triazine, thereby obtaining 2-ethoxy-4-amino-6-(1'-(2'-thianaphthenyl)ethylamino)-s-triazine (Compound 19). The structural formula and the analytical results of the compound as obtained above are shown in Tables 2 to 4.

TABLE 2

| Preparation Example No. | | Triazine Derivative | | | Analytical result | | | | |
|---|---|---|---|---|---|---|---|---|---|
| | | | Amount (g) | Yield (%) | Melting point (°C.) | Elemental analysis* (%) | | | |
| | | Name | | | | C | H | N | S |
| 1 | Compound 1 | 2-chloro-4-amino-6-[1'-(2'-benzofuranyl)ethylamino]-s-triazine | 27.5 | 95 | 128.2~129.5 | 54.0 (53.9) | 4.3 (4.2) | 23.9 (24.2) | — |

TABLE 2-continued

Triazine Derivative

| Preparation Example No. | Name | | Amount (g) | Yield (%) | Melting point (°C.) | Elemental analysis* (%) | | | |
|---|---|---|---|---|---|---|---|---|---|
| | | | | | | C | H | N | S |
| 2 | Compound 2 | 2-chloro-4-amino-6-[1'-(2'-benzofuranyl)propylamino]-s-triazine | 2.88 | 95 | 121.1~123.5 | 55.7 (55.4) | 4.5 (4.6) | 22.9 (23.1) | — |
| 3 | Compound 3 | 2-chloro-4-amino-6-[1'-(2'-(5'-chlorobenzofuranyl))ethylamino]-s-triazine | 3.18 | 93 | 190.7~191.2 | 48.4 (48.2) | 3.3 (3.4) | 22.0 (21.6) | — |
| 4 | Compound 4 | 2-chloro-4-amino-6-[1'-(3'-thianaphthenyl)ethylamino]-s-triazine | 2.84 | 93 | 193.4~193.8 | 50.8 (51.1) | 3.9 (4.0) | 23.1 (22.9) | 10.3 (10.5) |
| 5 | Compound 5 | 2-chloro-4-amino-6-[1'-(2'-thianaphthenyl)ethylamino]-s-triazine | 2.87 | 94 | 187.0~188.0 | 51.1 (51.1) | 3.9 (4.0) | 22.8 (22.9) | 10.5 (10.5) |
| 6 | Compound 6 | 2-chloro-4-amino-6-[1'-(2'-(2',3'-dihydrobenzofuranyl))ethylamino]-s-triazine | 2.71 | 93 | 199.3~200.5 | 53.6 (53.5) | 4.7 (4.8) | 24.2 (24.0) | — |
| 7 | Compound 7 | 2-methylthio-4-amino-6-[1'-(2'-benzofuranyl)ethylamino]-s-triazine | 27.1 | 90 | 116.3~117.3 | 55.8 (55.8) | 5.1 (5.0) | 22.9 (23.2) | 10.6 (10.6) |
| 8 | Compound 8 | 2-methylthio-4-amino-6-[1'-(2'-benzofuranyl)propylamino]-s-triazine | 2.87 | 91 | colorless resinoid form | 57.3 (57.1) | 5.5 (5.4) | 22.0 (22.2) | 10.1 (10.2) |
| 9 | Compound 9 | 2-methylthio-4-amino-6-[1'-(2'-(5'-chlorobenzofuranyl))ethylamino]-s-triazine | 3.12 | 93 | colorless resinoid form | 50.2 (50.1) | 4.3 (4.2) | 20.8 (20.9) | 9.3 (9.5) |
| 10 | Compound 10 | 2-methylthio-4-amino-6-[1'-(3'-thianaphthenyl)ethylamino]-s-triazine | 2.95 | 93 | colorless resinoid form | 52.8 (53.0) | 4.9 (4.8) | 22.2 (22.0) | 20.1 (20.2) |
| 11 | Compound 11 | 2-methylthio-4-amino-6-[1'-(2'-thianaphthenyl)ethylamino]-s-triazine | 2.92 | 92 | colorless resinoid form | 53.2 (53.0) | 4.6 (4.8) | 22.0 (22.0) | 20.1 (20.2) |
| 12 | Compound 12 | 2-methylthio-4-amino-6-[1'-(2'-(2',3'-dihydrobenzofuranyl))-ethylamino]-s-triazine | 2.76 | 91 | colorless resinoid form | 55.6 (55.4) | 5.5 (5.6) | 23.0 (23.1) | 10.7 (10.6) |
| 13 | Compound 13 | 2-ethylthio-4-amino-6-[1'-(2'-benzofuranyl)ethylamino]-s-triazine | 2.93 | 93 | 61.1~63.1 | 57.7 (57.1) | 5.5 (5.4) | 22.0 (22.2) | 10.1 (10.2) |
| 14 | Compound 14 | 2-ethylthio-4-amino-6-[1'-(2'-thianaphthenyl)ethylamino]-s-triazine | 3.05 | 92 | colorless resinoid form | 54.7 (54.4) | 5.0 (5.2) | 21.0 (21.1) | 19.4 (19.3) |
| 15 | Compound 15 | 2-methoxy-4-amino-6-[1'-(2'-benzofuranyl)ethylamino]-s-triazine | 2.62 | 92 | colorless resinoid form | 59.1 (58.9) | 5.2 (5.3) | 24.3 (24.5) | — |
| 16 | Compound 16 | 2-methoxy-4-amino-6-[1'-(2'-benzofuranyl)propylamino]-s-triazine | 2.72 | 91 | colorless resinoid form | 60.3 (60.2) | 5.5 (5.7) | 23.6 (23.4) | — |
| 17 | Compound 17 | 2-methoxy-4-amino-6-[1'-(2'-thianaphthenyl)ethylamino]-s-triazine | 2.77 | 92 | 156.4~157.2 | 55.8 (55.8) | 5.2 (5.0) | 23.1 (23.2) | 10.5 (10.6) |
| 18 | Compound 18 | 2-ethoxy-4-amino-6-[1'-(2'-benzofuranyl)ethylamino]-s-triazine | 2.75 | 92 | 161.4~162.7 | 60.1 (60.2) | 5.6 (5.7) | 23.6 (23.4) | — |
| 19 | Compound 19 | 2-ethoxy-4-amino-6-[1'-(2'-thianaphthenyl)ethylamino]-s-triazine | 2.87 | 91 | 202.4~203.0 | 57.3 (57.1) | 5.2 (5.4) | 22.1 (22.2) | 10.3 (10.2) |
| 20 | Compound 20 | 2-chloro-4-amino-6-[1'-(2'-(6'-methylbenzofuranyl))ethylamino]-s-triazine | 2.85 | 94 | 154.9~155.4 | 55.7 (55.4) | 4.5 (4.6) | 23.4 (23.1) | — |
| 21 | Compound 21 | 2-chloro-4-amino-6-[1'-(2'-(6'-methoxybenzofuranyl))ethylamino]-s-triazine | 2.94 | 92 | colorless resinoid form | 52.9 (52.6) | 4.3 (4.4) | 21.7 (21.9) | — |
| 22 | Compound 22 | 2-methylthio-4-amino-6-[1'-(2'-(6'-methylbenzofuranyl))ethylamino]-s-triazine | 2.90 | 92 | colorless resinoid form | 57.0 (57.1) | 5.5 (5.4) | 22.4 (22.2) | 10.0 (10.2) |
| 23 | Compound 23 | 2-methylthio-4-amino-6-[1'-(2'-(6'-methoxybenzofuranyl))ethylamino]-s-triazine | 2.98 | 90 | colorless resinoid form | 54.0 (54.4) | 5.3 (5.2) | 21.5 (21.1) | 9.9 (9.7) |

*A numeral in the brackets means the calculated value of the Elemental analysis.

TABLE 3

| Preparation Example No. | Name | Infrared Absorption Spectrum*[1] (cm$^{-1}$) | | | Proton Nuclear Magnetic Resonance Spectrum*[2] (ppm) |
|---|---|---|---|---|---|
| | | $NH_2$ | NH | s-triazine | |
| 1 | Compound 1 | 3510,3440 | 3320 | 1560 | 1.61(3H, d, —CH—C$\underline{H}_3$), 5.20~5.80(1H, m, —C$\underline{H}$—CH$_3$), 6.61(1H, s, —C$\underline{H}$=C$\diagup\diagdown$), 7.05~7.66 (4H, m, benzene ring) |
| 2 | Compound 2 | 3510,3420 | 3340 | 1560 | 0.96(3H, t, —CH$_2$—C$\underline{H}_3$), 1.81~2.14(2H, m, —C$\underline{H}_2$—CH$_3$), |

TABLE 3-continued

| Preparation Example No. | Name | Infrared Absorption Spectrum[*1] (cm$^{-1}$) NH$_2$ | NH | s-triazine | Proton Nuclear Magnetic Resonance Spectrum[*2] (ppm) |
|---|---|---|---|---|---|
| | | | | | 5.15~5.30(1H, m, —C$\underline{H}$—C$_2$H$_5$), 6.56(1H, s, —C$\underline{H}$=C$\diagup_\diagdown$), 7.12~7.56(4H, m, benzene ring) |
| 3 | Compound 3 | 3500,3440 | 3370 | 1580 | 1.59(3H, d, —CH—C$\underline{H_3}$), 5.31~5.51(1H, m, —C$\underline{H}$—CH$_3$), 6.50(1H, s, —C$\underline{H}$=C$\diagup_\diagdown$), 7.13~7.49(4H, m, benzene ring + —N$\underline{H}$) |
| 4 | Compound 4 | 3490,3430 | 3340 | 1580 | 1.60(3H, d, —CH—C$\underline{H_3}$), 1.45~1.70(1H, m, —C$\underline{H}$—CH$_3$), 7.24~7.92(6H, m, benzene ring + —C$\underline{H}$=C$\diagup_\diagdown$ + —N$\underline{H}$) |
| 5 | Compound 5 | 3490,3430 | 3340 | 1580 | 1.65(3H, d, —CH—C$\underline{H_3}$), 5.42~5.62(1H, m, —C$\underline{H}$—CH$_3$), 7.17~7.84(6H, m, benzene ring + —C$\underline{H}$=C$\diagup_\diagdown$ + —N$\underline{H}$) |
| 6 | Compound 6 | 3450,3350 | 3310 | 1570 | 1.25(3H, d, —CH—C$\underline{H_3}$), 2.81~3.35(2H, m, —C$\underline{H_2}$—CH—), 4.20~4.47, 4.67~4.91(each 1H, m, —CH$_2$—C$\underline{H}$—, —C$\underline{H}$—CH$_3$), 6.36~7.35(7H, m, benzene ring + —N$\underline{H_2}$ + N$\underline{H}$) |
| 7 | Compound 7[*3] | 3510,3440 3470,3340 | 3360 3270 | 1550 1540 | 1.61(3H, d, —CH—C$\underline{H_3}$), 2.37(3H, s, —SC$\underline{H_3}$), 5.20~5.79(1H, m, —$\underline{H}$—CH$_3$), 6.61(1H, s, —C$\underline{H}$=C$\diagup_\diagdown$), 7.05~7.65(4H, m, benzene ring) |
| 8 | Compound 8 | 3490,3410 | 3330 | 1540 | 0.98(3H, t, —CH$_2$—C$\underline{H_3}$), 1.76~2.10(2H, m, —C$\underline{H_2}$—CH$_3$), 2.45(3H, s, —SC$\underline{H_3}$), 6.56(1H, s, —C$\underline{H}$=C$\diagup_\diagdown$), 7.10~7.55(4H, m, benzene ring) |
| 9 | Compound 9 | 3500,3430 | 3330 | 1540 | 1.58(3H, d, —CH—C$\underline{H_3}$), 2.43(3H, s, —SC$\underline{H_3}$), 5.21~5.56(3H, m, —C$\underline{H}$—CH$_3$, N$\underline{H_2}$), 6.47(1H, s, —C$\underline{H}$=C$\diagup_\diagdown$), 7.15~7.45(3H, m, benzene ring) |
| 10 | Compound 10 | 3480,3420 | 3320 | 1540 | 1.65(3H, d, —CH—C$\underline{H_3}$), 2.38(3H, s, —SC$\underline{H_3}$), 5.42~5.74(2H, m, —C$\underline{H}$—CH$_3$ + N$\underline{H}$), 7.24~7.86(5H, m, —C$\underline{H}$=C$\diagup_\diagdown$ + bnzene ring) |
| 11 | Compound 11 | 3480,3400 | 3320 | 1530 | 1.61(3H, d, —CH—C$\underline{H_3}$), 2.42(3H, s, —SC$\underline{H_3}$), 5.46~5.68(1H, m, —C$\underline{H}$—CH$_3$), 7.06~7.76(5H, m, —C$\underline{H}$=C$\diagup_\diagdown$ + bnzene ring) |
| 12 | Compound 12 | broad | broad | 1550 | 1.19 + 1.35(3H, d+d, —CH—C$\underline{H_3}$), 2.42(3H, s, —SC$\underline{H_3}$), |

TABLE 3-continued

| Preparation Example No. | Name | Infrared Absorption Spectrum*1 (cm$^{-1}$) NH$_2$ | NH | s-triazine | Proton Nuclear Magnetic Resonance Spectrum*2 (ppm) |
|---|---|---|---|---|---|
| | | absorption | absorption | | 2.97~3.34(2H, m, —C$\underline{H_2}$—CH—), 4.21~4.50(1H, m, —CH$_2$—C$\underline{H}$), 4.75~4.90(1H, m, —C$\underline{H}$—CH$_3$), 6.71~7.28(4H, m, benzene ring) |
| 13 | Compound 13 | 3510,3440 | 3340 | 1540 | 1.30(3H, t, —SCH$_2$C$\underline{H_3}$), 1.58(3H, d, —CH—C$\underline{H_3}$), 3.02(2H, q, —SC$\underline{H_2}$CH$_3$), 5.18~5.56(3H, m, —C$\underline{H}$—CH$_3$ + —N$\underline{H_2}$), 6.53(1H, s, —C$\underline{H}$=C\<), 7.11~7.52(4H, m, benzene ring) |
| 14 | Compound 14 | 3500,3420 | 3340 | 1540 | 1.29(3H, t, —SCH$_2$C$\underline{H_3}$), 1.61(3H, d, —CH—C$\underline{H_3}$), 3.02(2H, q, —SC$\underline{H_2}$CH$_3$), 5.46~5.65(1H, m, —C$\underline{H}$—CH$_3$), 7.04~7.80(5H, m, —C$\underline{H}$=C\< + benzene ring) |
| 15 | Compound 15 | 3500,3420 | 3340 | 1570 | 1.59(3H, d, —CH—C$\underline{H_3}$), 3.85(3H, s, —OC$\underline{H_3}$), 5.29~5.64(3H, m, —C$\underline{H}$—CH$_3$ + —N$\underline{H_2}$), 6.52(1H, s, —C$\underline{H}$=C\<), 7.05~7.54(4H, m, benzene ring) |
| 16 | Compound 16 | 3500,3420 | 3340 | 1580 | 0.96(3H, t, —CH$_2$—C$\underline{H_3}$), 1.80~2.15(2H, m, —C$\underline{H_2}$—CH$_3$), 3.86(3H, d, —OC$\underline{H_3}$), 5.15~5.42(3H, m, —C$\underline{H}$—C$_2$H$_5$ + —N$\underline{H_2}$), 6.56(1H, s, —C$\underline{H}$=C\<), 7.11~7.52(4H, m, benzene ring) |
| 17 | Compound 17 | 3500,3410 | 3320 | 1580 | 1.61(3H, d, —CH—C$\underline{H_3}$), 3.86(3H, s, —OC$\underline{H_3}$), 5.47~5.69(1H, m, —C$\underline{H}$—CH$_3$), 7.04~7.79(5H, m, —C$\underline{H}$=C\< + benzene ring) |
| 18 | Compound 18 | 3500,3320 | 3340 | 1570 | 1.31(3H, t, —OCH$_2$C$\underline{H_3}$), 1.57(3H, d, —CH—C$\underline{H_3}$), 4.13~4.41(2H, q, —OC$\underline{H_2}$CH$_3$), 5.28~5.57(3H, m, —C$\underline{H}$—CH$_3$ + N$\underline{H_2}$), 6.54(1H, s, —C$\underline{H}$=C\<), 7.11~7.52(4H, m, benzene ring) |
| 19 | Compound 19 | broad absorption | broad absorption | 1560 | 1.27(3H, t, —OCH$_2$C$\underline{H_3}$), 1.62(3H, d, —CH—C$\underline{H_3}$), 4.27(2H, q, —OC$\underline{H_2}$CH$_3$), 5.47~5.63(1H, m, —C$\underline{H}$—CH$_3$), 7.11~7.79(6H, m, benzene ring + —C$\underline{H}$=C\< + N$\underline{H}$) |
| 20 | Compound 20 | 3510,3440 | 3330 | 1570 | 1.60(3H, d, —CH—C$\underline{H_3}$), 2.42(3H, s, C$\underline{H_3}$—⌬—), 5.30~5.55(1H, m, —C$\underline{H}$—CH$_3$), 6.47(1H, s, —C$\underline{H}$=C\<), 7.02~7.35(3H, m, benzene ring) |
| 21 | Compound 21 | 3500,3430 | 3350 | 1570 | 1.60(3H, d, —CH—C$\underline{H_3}$), 3.82(3H, s, —OC$\underline{H_3}$) |

TABLE 3-continued

| Preparation Example No. | Name | Infrared Absorption Spectrum*1 (cm$^{-1}$) | | | Proton Nuclear Magnetic Resonance Spectrum*2 (ppm) |
|---|---|---|---|---|---|
| | | NH$_2$ | NH | s-triazine | |
| | | | | | 5.29~5.56(1H, m, —C$\underline{H}$—CH$_3$), 6.48(1H, s, —C$\underline{H}$=C〈 ) |
| | | | | | 6.72~7.43(3H, m, benzene ring) |
| 22 | Compound 22 | 3500,3430 | 3340 | 1540 | |
| | | | | | 1.57(3H, d, —CH—C$\underline{H_3}$), 2.42(6H, s, —SC$\underline{H_3}$+C$\underline{H_3}$—⟨○⟩—) |
| | | | | | 5.22~5.52(3H, m, —C$\underline{H}$—CH$_3$+N$\underline{H_2}$), 6.47(1H, s, —C$\underline{H}$=C〈 ) |
| | | | | | 7.02~7.35(3H, m, benzene ring) |
| 23 | Compound 23 | 3500,3430 | 3350 | 1540 | 1.58(3H, d, CH—C$\underline{H_3}$), 2.41(3H, s, —SC$\underline{H_3}$), |
| | | | | | 3.81(3H, s, —OC$\underline{H_3}$), 5.20~5.60(3H, m, —C$\underline{H}$—CH$_3$+N$\underline{H_2}$) |
| | | | | | 6.46(1H, s, —C$\underline{H}$=C〈 )6.70~7.45(3H, m, benzene ring) |

*1Measured by the potassium bromide tablet method.
*2Solvent: chloroform-D$_1$ (with exceptions that acetone-D$_6$ was used in Compounds 1 and 8, and a mixture of chloroform-D$_1$ and dimethyl sulfoxide-D$_6$ was used in Compounds 3 to 6 and 19). Internal standard: tetramethylsilane
*3In the column of Infrared Absorption Spectrum, the values appearing in the upper line indicate those of the non-crystalline form and the values appearing in the lower line, those of the crystalline form.

TABLE 4

| Preparation Example No. | Triazine Derivative | | | |
|---|---|---|---|---|
| | Name | Structure | Molecular formula | Molecular weight |
| 1 | Compound 1 | [structure] | C$_{13}$H$_{12}$N$_5$OCl | 289.7 |
| 2 | Compound 2 | [structure] | C$_{14}$H$_{14}$N$_5$OCl | 303.7 |
| 3 | Compound 3 | [structure] | C$_{13}$H$_{11}$N$_5$OCl$_2$ | 324.2 |
| 4 | Compound 4 | [structure] | C$_{13}$H$_{12}$N$_5$SCl | 305.8 |
| 5 | Compound 5 | [structure] | C$_{13}$H$_{12}$N$_5$SCl | 305.8 |

TABLE 4-continued

| Preparation Example No. | Triazine Derivative Name | Molecular formula | Molecular weight |
|---|---|---|---|
| 6 | Compound 6 | C$_{13}$H$_{14}$N$_5$OCl | 291.7 |
| 7 | Compound 7 | C$_{14}$H$_{15}$N$_5$OS | 301.4 |
| 8 | Compound 8 | C$_{15}$H$_{17}$N$_5$OS | 315.4 |
| 9 | Compound 9 | C$_{14}$H$_{14}$N$_5$OSCl | 335.8 |
| 10 | Compound 10 | C$_{14}$H$_{15}$N$_5$S$_2$ | 317.4 |
| 11 | Compound 11 | C$_{14}$H$_{15}$N$_5$S$_2$ | 317.4 |
| 12 | Compound 12 | C$_{14}$H$_{17}$N$_5$OS | 303.4 |
| 13 | Compound 13 | C$_{15}$H$_{17}$N$_2$OS | 315.4 |
| 14 | Compound 14 | C$_{15}$H$_{17}$N$_5$S$_2$ | 331.5 |

TABLE 4-continued

| Preparation Example No. | Triazine Derivative Name | Structure | Molecular formula | Molecular weight |
|---|---|---|---|---|
| 15 | Compound 15 | 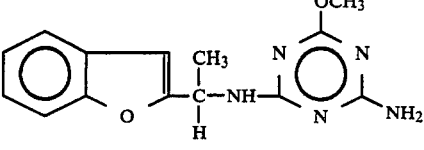 | $C_{14}H_{15}N_5O_2$ | 285.3 |
| 16 | Compound 16 | 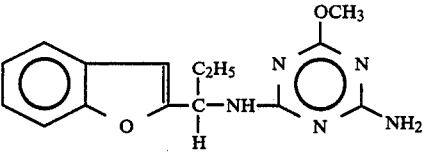 | $C_{15}H_{17}N_5S_2$ | 299.3 |
| 17 | Compound 17 | 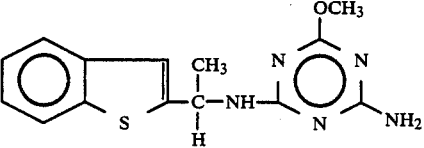 | $C_{14}H_{15}N_5SO$ | 301.4 |
| 18 | Compound 18 | 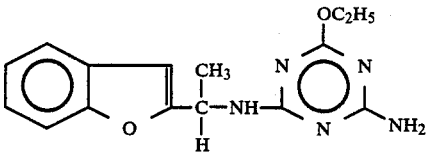 | $C_{15}H_{17}N_5O_2$ | 299.3 |
| 19 | Compound 19 | 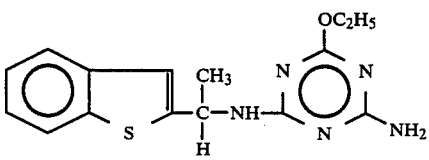 | $C_{15}H_{17}N_5SO$ | 315.4 |
| 20 | Compound 20 | 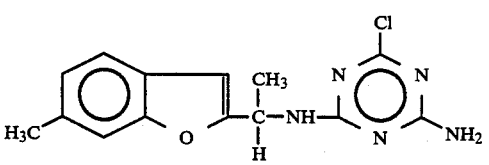 | $C_{14}H_{14}N_5OCl$ | 303.7 |
| 21 | Compound 21 | 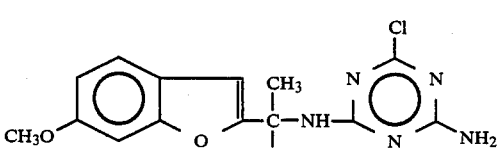 | $C_{14}H_{14}N_5O_2Cl$ | 319.7 |
| 22 | Compound 22 | 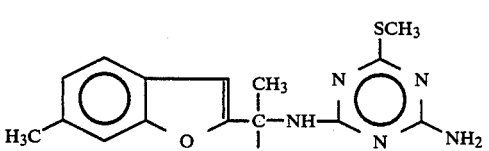 | $C_{15}H_{17}N_5OS$ | 315.4 |
| 23 | Compound 23 | 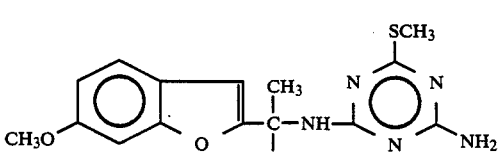 | $C_{15}H_{17}N_5O_2S$ | 331.4 |

EXAMPLES 1–19 AND 28–31

(1) Preparation of herbicide:

97 parts by weight of talc (trade name: Zeaklite) as carrier, 1.5 parts by weight of alkylarylsulfonate as surfactant (trade name: Neo pelex, manufactured by Kao-Atlas KK) and 1.5 parts by weight of a mixture of nonion type and anion type surfactant (trade name: Sorpol 800A, manufactured by Toho Kagaku Kogyo KK) were homogeneously ground and mixed to obtain a carrier for a wettable powder.

A herbicidal wettable powder was prepared by grinding and mixing homogeneously 90 parts by weight of the above obtained carrier for the wettable powder with 10 parts by weight of one of the triazine derivatives prepared as reported in the Preparation Examples 1-19 and 28-31.

(2) Results of biological tests:
Treatment under submerged condition

A 1/15500-are porcelain pot was filled with the soil of a paddy field and seeds of *Echinochloa crus-galli* L., *Cyperus difformis* L., *Rotala indica* (Willd.) Koehne va. *uligirosa* (Miq.) Koehne., *Scirpus juncoides* Roxb. var. Hotarui Ohwi and *Monochoria vaginalis* Presl var. *plantaginea* (Roxb.) Solms-Laub. were sown uniformly in the upper layer of the soil. And then the tubers of *Cyperus serotinus* Rottb. and *Sagittaria pygmaea* Miq. were planted in the soil, thereafter young rice plants of the second-leaf stage were transplanted.

When the weeds were germinated, a predetermined amount of a diluted solution of a herbicide prepared as reported in paragraph (1) hereinbefore was uniformly applied dropwise to the surface of the water and then the pot was kept in a green-house and sprinkled with water at appropriate time intervals.

Table 5 reports the evaluation of the herbicidal effect and the phytotoxicity to the paddy rice plants at 20 days after application of the herbicide. In Table 5, the amount of the herbicide means the amount of the active component, 100 grams/10 ares. The phytotoxicity and herbicidal effect were evaluated respectively according to the following scale by determining the dry weight.

| | Phytotoxicity to the paddy rice plants: | |
|---|---|---|
| 0 | ratio to an untreated pot | 100% |
| 1 | " | 95-99% |
| 2 | " | 90-94% |
| 3 | " | 80-89% |
| 4 | " | 60-79% |
| 5 | " | 50-69% |
| | Herbicidal effect: | |
| 0 | ratio to the untreated pot | 100% |
| 1 | " | 61-99% |
| 2 | " | 21-60% |
| 3 | " | 11-20% |
| 4 | " | 1-10% |
| 5 | " | 0% |

COMPARATIVE EXAMPLE 1

The same procedure as in Example 1 was carried out except that 2-methylthio-4,6-bis(ethylamino)-s-triazine (common name: Simetryn) shown in the following formula (A) was used in place of the triazine derivative prepared as reported in the Preparation Example 1. The results are shown in Table 5.

COMPARATIVE EXAMPLE 2

The same procedure as in Example 1 was carried out except that 2-methylthio-4-methylamino-6-(α,α-dimethylbenzylamino)-s-triazine (Japanese Patent Publication No. 8261/1974) shown in the following formula (B) was used in place of the triazine derivative prepared as reported in the Preparation Example 1. The results are shown in Table 5.

COMPARATIVE EXAMPLE 3

The same procedure as in Example 1 was carried out except that 2-chloro-4-isopropylamino-6-(α,α-dimethylbenzylamino)-s-triazine (Japanese Patent Publication No. 8262/1974) shown in the following formula (C) was used in place of the triazine derivative prepared as reported in the Preparation Example 1. The results shown in Table 5.

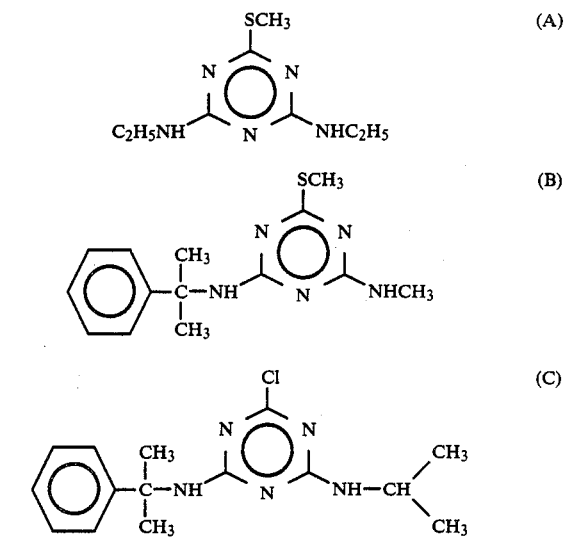

EXAMPLES 20 TO 27, 32 AND COMPARATIVE EXAMPLE 4

(Foliage Treatment Test)

Upland field soil was packed in a 1/2000 are wagner pot. Weed seeds of velvet-leaf, common blackjack (*Bideus pilosa* L.), amaranth (*Amaranthus cruentus* L.), sicklepod, tall morningglory, and crop seeds of corns, grain sorghum, wheat, barley and oats (*Avera sativa* L.) were sowed in the upland field soil. After covering with soil, the seeds were grown in a green-house. At the time of the first- or second-leaf stage of the weeds and the third-leaf stage of the crops, a predetermined amount of each herbicide as obtained in the above examples was suspended in water and uniformly sprayed to the foliage portion in an amount corresponding to 100 liters per 10 ares. Thereafter, the weeds and crops were allowed to grow in the green-house. In 20 days after the treatment, the phytotoxicity to crops and the herbicidal effect were determined according to the criteria as shown below. The results are shown in Table 6.

The foliage treatment test as described above was repeated with the exception that 2-chloro-4-isopropylamino-6-ethylamino-s-triazine (common name: "Atrazine") was used as a herbicide. The results are shown in Table 6.

| Extent of Herbicidal effect | Herbicidal effect (weed-killing rate) |
|---|---|
| 0 | less than 5% (Almost no herbicidal effect) |
| 1 | 5-20% |
| 2 | 20-40% |
| 3 | 40-70% |
| 4 | 70-90% |
| 5 | more than 90% (Almost all |

-continued

| Extent of Herbicidal effect | Herbicidal effect (weed-killing rate) weeds die completely) |
|---|---|

The above weed-killing rate was calculated from the following equation.

Weed Killing Rate (%) =

$$\left(1 - \frac{\text{Fresh weight of aerial part of weeds treated with Herbicide}}{\text{Fresh weight of aerial part of weeds not treated with Herbicide}}\right) \times 100$$

Extent of phytotoxicity to the crops:
0: No injury
1: Very slight injury
2: Slight injury
3: Moderate injury
4: Severe injury
5: Almost all plants died

TABLE 5

| No. | Compound as effective component | Amount of herbicide (gram/10 ares) | Echinochloa crus-galli L. | Cyperus serotinus Rottb. | Scirpus juncoides Roxb. var. Hotarui Ohwi | Cyperus difformis L. | Annual broadleaf weeds | Sagittaria pygmaea Miq. | Phytotoxicity to the paddy rice plants |
|---|---|---|---|---|---|---|---|---|---|
| Example 1 | Compound 1 | 100 | 5 | 5 | 5 | 5 | 5 | 5 | 0 |
|  |  | 50 | 5 | 5 | 5 | 5 | 5 | 5 | 0 |
| Example 2 | Compound 2 | 100 | 5 | 5 | 5 | 5 | 5 | 5 | 0 |
|  |  | 50 | 5 | 5 | 5 | 5 | 5 | 5 | 0 |
| Example 4 | Compound 4 | 100 | 5 | 5 | 4 | 5 | 5 | 3 | 0 |
| Example 5 | Compound 5 | 100 | 5 | 5 | 4 | 5 | 5 | 5 | 0 |
|  |  | 50 | 5 | 5 | 3 | 5 | 5 | 4 | 0 |
| Example 6 | Compound 6 | 100 | 5 | 3 | 3 | 5 | 5 | 3 | 0 |
| Example 7 | Compound 7 | 100 | 5 | 5 | 5 | 5 | 5 | 5 | 0 |
|  |  | 50 | 5 | 5 | 5 | 5 | 5 | 5 | 0 |
| Example 8 | Compound 8 | 100 | 5 | 5 | 5 | 5 | 5 | 5 | 0 |
|  |  | 50 | 5 | 5 | 5 | 5 | 5 | 5 | 0 |
| Example 9 | Compound 9 | 100 | 5 | 5 | 5 | 5 | 5 | 4 | 0 |
|  |  | 50 | 5 | 5 | 5 | 5 | 5 | 3 | 0 |
| Example 10 | Compound 10 | 100 | 5 | 5 | 5 | 5 | 5 | 5 | 0 |
|  |  | 50 | 5 | 5 | 5 | 5 | 5 | 5 | 0 |
| Example 11 | Compound 11 | 100 | 5 | 5 | 3 | 5 | 5 | 5 | 0 |
|  |  | 50 | 5 | 5 | 3 | 5 | 5 | 3 | 0 |
| Example 12 | Compound 12 | 100 | 5 | 4 | 4 | 5 | 5 | 4 | 0 |
| Example 13 | Compound 13 | 100 | 5 | 5 | 5 | 5 | 5 | 5 | 0 |
|  |  | 50 | 5 | 5 | 5 | 5 | 5 | 5 | 0 |
| Example 14 | Compound 14 | 100 | 5 | 5 | 5 | 5 | 5 | 5 | 0 |
|  |  | 50 | 5 | 5 | 4 | 5 | 5 | 4 | 0 |
| Example 15 | Compound 15 | 100 | 5 | 5 | 5 | 5 | 5 | 5 | 0 |
|  |  | 50 | 5 | 5 | 5 | 5 | 5 | 5 | 0 |
| Example 16 | Compound 16 | 100 | 5 | 5 | 5 | 5 | 5 | 5 | 0 |
|  |  | 50 | 5 | 5 | 5 | 5 | 5 | 5 | 0 |
| Example 17 | Compound 17 | 100 | 5 | 5 | 5 | 5 | 5 | 5 | 0 |
|  |  | 50 | 5 | 5 | 5 | 5 | 5 | 5 | 0 |
| Example 18 | Compound 18 | 100 | 5 | 4 | 4 | 5 | 5 | 4 | 0 |
| Example 19 | Compound 19 | 100 | 5 | 4 | 4 | 5 | 5 | 4 | 0 |
| Comparative Example 1 | Formula [A] | 100 | 5 | 2 | 3 | 5 | 5 | 3 | 2 |
|  |  | 50 | 1 | 0 | 0 | 5 | 5 | 0 | 0 |
| Comparative Example 2 | Formula [B] | 100 | 4 | 0 | 1 | 5 | 5 | 0 | 0 |
| Comparative Example 3 | Formula [C] | 100 | 5 | 5 | 5 | 5 | 5 | 5 | 0 |
| Example 28 | Compound 20 | 100 | 5 | 5 | 5 | 5 | 5 | 5 | 0 |
|  |  | 50 | 5 | 5 | 5 | 5 | 5 | 5 | 0 |
| Example 29 | Compound 21 | 100 | 5 | 5 | 5 | 5 | 5 | 5 | 0 |
|  |  | 50 | 5 | 5 | 5 | 5 | 5 | 5 | 0 |
| Example 30 | Compound 22 | 100 | 5 | 5 | 5 | 5 | 5 | 5 | 0 |
|  |  | 50 | 5 | 5 | 5 | 5 | 5 | 5 | 0 |
| Example 31 | Compound 23 | 100 | 5 | 5 | 5 | 5 | 5 | 5 | 0 |
|  |  | 50 | 5 | 5 | 5 | 5 | 5 | 5 | 0 |

TABLE 6

| No. | Compound as effective component | Amount of herbicide (gram/10 ares) | Phytotoxicity | | | | | Herbicidal effect | | | | |
|---|---|---|---|---|---|---|---|---|---|---|---|---|
| | | | corn*1 | grain sorghum*2 | wheat*3 | barley*4 | oats*5 | velvet leaf*6 | common black-jack*7 | ama-ranth*8 | sickle-pod*9 | tall morning glory*10 |
| Example 20 | Compound 1 | 400 | 0 | 0 | 0 | 0 | 0 | 5 | 5 | 5 | 5 | 5 |
|  |  | 200 | 0 | 0 | 0 | 0 | 0 | 5 | 5 | 5 | 5 | 5 |
|  |  | 100 | 0 | 0 | 0 | 0 | 0 | 5 | 5 | 5 | 4 | 5 |
|  |  | 50 | 0 | 0 | 0 | 0 | 0 | 3 | 5 | 5 | 3 | 5 |
|  |  | 25 | 0 | 0 | 0 | 0 | 0 | 3 | 5 | 5 | 2 | 5 |
|  |  | 12.5 | 0 | 0 | 0 | 0 | 0 | 1 | 4 | 5 | 2 | 3 |
| Example 21 | Compound 5 | 400 | 0 | 0 | 0 | 0 | 0 | 5 | 5 | 5 | 5 | 5 |

TABLE 6-continued

| No. | Compound as effective component | Amount of herbicide (gram/10 ares) | Phytotoxicity |||||  Herbicidal effect |||||
|---|---|---|---|---|---|---|---|---|---|---|---|---|
| | | | corn*1 | grain sorghum*2 | wheat*3 | barley*4 | oats*5 | velvet leaf*6 | common black-jack*7 | amaranth*8 | sickle-pod*9 | tall morning glory*10 |
| | | 200 | 0 | 0 | 0 | 0 | 0 | 5 | 5 | 5 | 5 | 5 |
| | | 100 | 0 | 0 | 0 | 0 | 0 | 5 | 5 | 5 | 4 | 5 |
| | | 50 | 0 | 0 | 0 | 0 | 0 | 5 | 5 | 5 | 3 | 5 |
| | | 25 | 0 | 0 | 0 | 0 | 0 | 3 | 5 | 5 | 3 | 5 |
| | | 12.5 | 0 | 0 | 0 | 0 | 0 | 2 | 4 | 5 | 2 | 4 |
| Example 22 | Compound 6 | 400 | 0 | 0 | 0 | 0 | 0 | 5 | 5 | 5 | 5 | 5 |
| | | 200 | 0 | 0 | 0 | 0 | 0 | 5 | 5 | 5 | 5 | 5 |
| | | 100 | 0 | 0 | 0 | 0 | 0 | 5 | 5 | 5 | 4 | 5 |
| | | 50 | 0 | 0 | 0 | 0 | 0 | 5 | 5 | 5 | 3 | 5 |
| | | 25 | 0 | 0 | 0 | 0 | 0 | 5 | 5 | 5 | 3 | 5 |
| | | 12.5 | 0 | 0 | 0 | 0 | 0 | 3 | 5 | 5 | 1 | 3 |
| Example 23 | Compound 7 | 400 | 0 | 0 | 0 | 0 | 0 | 5 | 5 | 5 | 5 | 5 |
| | | 200 | 0 | 0 | 0 | 0 | 0 | 5 | 5 | 5 | 5 | 5 |
| | | 100 | 0 | 0 | 0 | 0 | 0 | 5 | 5 | 5 | 5 | 5 |
| | | 50 | 0 | 0 | 0 | 0 | 0 | 5 | 5 | 5 | 5 | 5 |
| | | 25 | 0 | 0 | 0 | 0 | 0 | 5 | 5 | 5 | 5 | 5 |
| | | 12.5 | 0 | 0 | 0 | 0 | 0 | 5 | 5 | 5 | 5 | 5 |
| Example 24 | Compound 10 | 400 | 0 | 0 | 0 | 0 | 0 | 5 | 5 | 5 | 5 | 5 |
| | | 200 | 0 | 0 | 0 | 0 | 0 | 5 | 5 | 5 | 5 | 5 |
| | | 100 | 0 | 0 | 0 | 0 | 0 | 5 | 5 | 5 | 5 | 5 |
| | | 50 | 0 | 0 | 0 | 0 | 0 | 5 | 5 | 5 | 4 | 5 |
| | | 25 | 0 | 0 | 0 | 0 | 0 | 5 | 4 | 5 | 3 | 5 |
| | | 12.5 | 0 | 0 | 0 | 0 | 0 | 3 | 4 | 4 | 3 | 3 |
| Example 25 | Compound 11 | 400 | 0 | 0 | 0 | 0 | 0 | 5 | 5 | 5 | 5 | 5 |
| | | 200 | 0 | 0 | 0 | 0 | 0 | 5 | 5 | 5 | 5 | 5 |
| | | 100 | 0 | 0 | 0 | 0 | 0 | 5 | 5 | 5 | 5 | 5 |
| | | 50 | 0 | 0 | 0 | 0 | 0 | 5 | 5 | 5 | 5 | 5 |
| | | 25 | 0 | 0 | 0 | 0 | 0 | 5 | 5 | 5 | 5 | 5 |
| | | 12.5 | 0 | 0 | 0 | 0 | 0 | 5 | 5 | 5 | 5 | 5 |
| Example 26 | Compound 12 | 400 | 0 | 0 | 0 | 0 | 0 | 5 | 5 | 5 | 5 | 5 |
| | | 200 | 0 | 0 | 0 | 0 | 0 | 5 | 5 | 5 | 5 | 5 |
| | | 100 | 0 | 0 | 0 | 0 | 0 | 5 | 5 | 5 | 5 | 5 |
| | | 50 | 0 | 0 | 0 | 0 | 0 | 5 | 5 | 5 | 5 | 5 |
| | | 25 | 0 | 0 | 0 | 0 | 0 | 5 | 5 | 5 | 5 | 5 |
| | | 12.5 | 0 | 0 | 0 | 0 | 0 | 5 | 5 | 5 | 5 | 5 |
| Example 27 | Compound 15 | 400 | 0 | 0 | 0 | 0 | 0 | 5 | 5 | 5 | 5 | 5 |
| | | 200 | 0 | 0 | 0 | 0 | 0 | 5 | 5 | 5 | 5 | 5 |
| | | 100 | 0 | 0 | 0 | 0 | 0 | 5 | 5 | 5 | 5 | 5 |
| | | 50 | 0 | 0 | 0 | 0 | 0 | 5 | 5 | 5 | 5 | 5 |
| | | 25 | 0 | 0 | 0 | 0 | 0 | 5 | 5 | 5 | 5 | 5 |
| | | 12.5 | 0 | 0 | 0 | 0 | 0 | 4 | 5 | 5 | 5 | 5 |
| Example 32 | Compound 22 | 400 | 0 | 0 | 0 | 0 | 0 | 5 | 5 | 5 | 5 | 5 |
| | | 200 | 0 | 0 | 0 | 0 | 0 | 5 | 5 | 5 | 5 | 5 |
| | | 100 | 0 | 0 | 0 | 0 | 0 | 5 | 5 | 5 | 5 | 5 |
| | | 50 | 0 | 0 | 0 | 0 | 0 | 5 | 5 | 5 | 5 | 5 |
| | | 25 | 0 | 0 | 0 | 0 | 0 | 5 | 5 | 5 | 5 | 5 |
| | | 12.5 | 0 | 0 | 0 | 0 | 0 | 5 | 5 | 5 | 5 | 5 |
| Comparative Example 4 | Atrazine*11 | 400 | 0 | 0 | 5 | 4 | 5 | 5 | 5 | 5 | 5 | 5 |
| | | 200 | 0 | 0 | 4 | 4 | 5 | 5 | 5 | 5 | 4 | 5 |
| | | 100 | 0 | 0 | 4 | 3 | 4 | 5 | 5 | 5 | 1 | 5 |
| | | 50 | 0 | 0 | 1 | 1 | 2 | 3 | 5 | 5 | 0 | 5 |
| | | 25 | 0 | 0 | 0 | 0 | 0 | 1 | 1 | 5 | 0 | 5 |
| | | 12.5 | 0 | 0 | 0 | 0 | 0 | 0 | 1 | 4 | 0 | 3 |

Botanical name
*1 *Zea mays* L.
*2 *Sorghum bicolor* (L.)Moeuch.
*3 *Triticum aestivum* L.
*4 *Hordeum vulgare* L. emend. Lamark
*5 *Avera sativa* L.
*6 *Abutilon theophrasti* Medik.
*7 *Bidens pilosa* L.
*8 *Amaranthus cruentus* L.
*9 *Cassia obtusifolia* L.
*10 *Ipomoea purpurea* (L.)Roth

*11 The structure of Atrazine is as follows

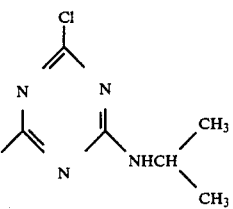

What is claimed is:
1. A triazine derivative represented by the formula:

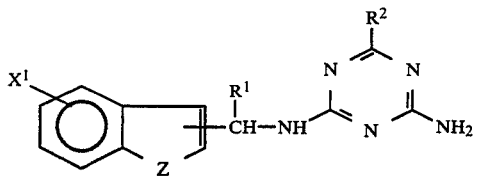

or the formula:

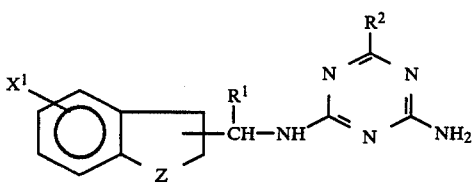

(wherein $X^1$ represents a hydrogen atom, a halogen atom, an alkyl group having 1 to 4 carbon atoms or an alkoxyl group having 1 to 4 carbon atoms, Z represents an oxygen atom or a sulfur atom, $R^1$ represents an alkyl group having 1 to 4 carbon atom, and $R^2$ represents a halogen atom, an alkylthio group having 1 to 4 carbon atoms, or an alkoxyl group having 1 to 4 carbon atoms).

2. The triazine derivative as claimed in claim 1, wherein $R^1$ represents a methyl group, and $R^2$ represents a methylthio group.

3. The triazine derivative as claimed in claim 1, wherein $R^1$ represents a methyl group, and $R^2$ represents a methoxy group.

4. The triazine derivative of claim 1 designated as 2-chloro-4-amino-6-[1'-(2'-benzofuranyl)ethylamino]-s-triazine.

5. The triazine derivative of claim 1 designated as 2-chloro-4-amino-6-[1'-(2'-benzofuranyl)propylamino]-s-triazine.

6. The triazine derivative of claim 1 designated as 2-chloro-4-amino-6-[1'-(2'-(5'-chlorobenzofuranyl))ethylamino-s-triazine.

7. The triazine derivative of claim 1 designated as 2-chloro-4-amino-6-[1'-(3'-thianaphthenyl)ethylamino]-s-triazine.

8. The triazine derivative of claim 1 designated as 2-chloro-4-amino-6-[1'-(2'-thianaphthenyl)ethylamino]-s-triazine.

9. The triazine derivative of claim 1 designated as 2-chloro-4-amino-6-[1'-(2'-(2',3'-dihydrobenzofuranyl))ethylamino]-s-triazine.

10. The triazine derivative of claim 1 designated as 2-methylthio-4-amino-6-[1'-(2'-benzofuranyl)ethylamino]-s-triazine.

11. The triazine derivative of claim 1 designated as 2-methylthio-4-amino-6-[1'-(2'-benzofuranyl)propylamino]-s-triazine.

12. The triazine derivative of claim 1 designated as 2-methylthio-4-amino-6-[1'-(2'-(5'-chlorobenzofuranyl))ethylamino]-s-triazine.

13. The triazine derivative of claim 1 designated as 2-methylthio-4-amino-6-[1'-(3'-trianaphthenyl)ethylamino]-s-triazine.

14. The triazine derivative of claim 1 designated as 2-methylthio-4-amino-6-[1'-(2'-thianaphthenyl)ethylamino]-s-triazine.

15. The triazine derivative of claim 1 designated as 2-methylthio-4-amino-6-[1'-(2'-(2',3'-dihydrobenzofuranyl))ethylamino]-s-triazine.

16. The triazine derivative of claim 1 designated as 2-ethylthio-4-amino-6-[1'-(2'-benzofuranyl)ethylamino]-s-triazine.

17. The triazine derivative of claim 1 designated as 2-ethylthio-4-amino-6-[1'-(2'-thianaphthenyl)ethylamino]-s-triazine.

18. The triazine derivative of claim 1 designated as 2-methoxy-4-amino-6-[1'-(2'-benzofuranyl)ethylamino]-s-triazine.

19. The triazine derivative of claim 1 designated as 2-methoxy-4-amino-6-[1'-(2'-benzofuranyl)propylamino]-s-triazine.

20. The triazine derivative of claim 1 designated as 2-methoxy-4-amino-6-[1'-(2'-thianaphthenyl)ethylamino]-s-triazine.

21. The triazine derivative of claim 1 designated as 2-ethoxy-4-amino-6-[1'-(2'-benzofuranyl)ethylamino]-s-triazine.

22. The triazine derivative of claim 1 designated as 2-ethoxy-4-amino-6-[1'-(2'-thianaphthenyl)ethylamino]-s-triazine.

23. The triazine derivative of claim 1 designated as 2-chloro-4-amino-6-[1'-(2'-(6'-methylbenzofuranyl))ethylamino]-s-triazine.

24. The triazine derivative of claim 1 designated as 2-chloro-4-amino-6-[1'-(2'-(6'-methoxybenzofuranyl))ethylamino]-s-triazine.

25. The triazine derivative of claim 1 designated as 2-methylthio-4-amino-6-[1'-(2'-(6'-methylbenzofuranyl))ethylamino]-s-triazine.

26. The triazine derivative of claim 1 designated as 2-methylthio-4-amino-6-[1'-(2'-(6'-methoxybenzofuranyl))ethylamino]-s-triazine.

27. A herbicidal composition comprising (i) a herbicidal carrier, and (ii) a herbicidally effective amount of triazine derivative represented by the formula:

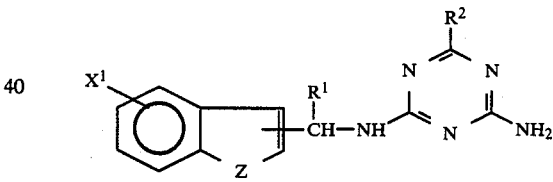

or the formula:

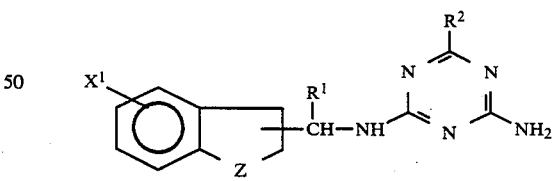

wherein $X^1$ represents a hydrogen atom, a halogen atom an alkyl group having 1 to 4 carbon atoms or an alkoxyl group having 1 to 4 carbon atoms, Z represents an oxygen atom or a sulfur atom, $R^1$ represents an alkyl group having 1 to 4 carbon atoms, and $R^2$ represents a halogen atom, an alkylthio group having 1 to 4 carbon atoms, or an alkoxyl group having 1 to 4 carbon atoms.

28. The herbicidal composition as claimed in claim 27, wherein $R^1$ represents a methyl group and $R^2$ represents a methylthio group.

29. The herbicidal composition as claimed in claim 27, wherein $R^1$ represents a methyl group and $R^2$ represents a methoxy group.

* * * * *